US012702496B2

(12) United States Patent
Shachaf et al.

(10) Patent No.: US 12,702,496 B2
(45) Date of Patent: Aug. 11, 2026

(54) SYSTEMS AND METHODS FOR ASSESSING TISSUE REMODELING

(71) Applicant: Orlucent, Inc., Los Gatos, CA (US)

(72) Inventors: Catherine M. Shachaf, Los Gatos, CA (US); Amit Shachaf, Los Gatos, CA (US); Kevin Manbeck, Los Gatos, CA (US)

(73) Assignee: Orlucent, Inc., Los Gatos, CA (US)

( * ) Notice: Subject to any disclaimer, the term of this patent is extended or adjusted under 35 U.S.C. 154(b) by 186 days.

(21) Appl. No.: 18/342,974

(22) Filed: Jun. 28, 2023

(65) Prior Publication Data

US 2024/0173084 A1 May 30, 2024

Related U.S. Application Data

(63) Continuation of application No. PCT/US2021/065470, filed on Dec. 29, 2021.

(Continued)

(51) Int. Cl.
*A61B 34/00* (2016.01)
*A61B 5/00* (2006.01)

(Continued)

(52) U.S. Cl.
CPC ............ *A61B 34/25* (2016.02); *A61B 5/0035* (2013.01); *A61B 5/0071* (2013.01);

(Continued)

(58) Field of Classification Search
CPC ..... A61B 34/25; A61B 5/0035; A61B 5/0071; A61B 5/0077; A61B 5/444; A61B 5/7275;

(Continued)

(56) References Cited

U.S. PATENT DOCUMENTS

| | | | |
|---|---|---|---|
| 4,239,390 | A | 12/1980 | Scherer |
| 4,560,252 | A | 12/1985 | Mori |

(Continued)

FOREIGN PATENT DOCUMENTS

| | | | |
|---|---|---|---|
| AU | 6374098 | B2 | 6/1998 |
| AU | 728668 | B2 | 1/2001 |

(Continued)

OTHER PUBLICATIONS

Anikijenko, Peter, et al. In Vivo Detection of Small Subsurface Melanomas in Athymic Mice Using Noninvasive Fiber Optic Confocal Imaging. The Society for Investigative Dermatology, vol. 117, 1142-1448 (2001).

(Continued)

*Primary Examiner* — Peter H Choi
*Assistant Examiner* — Kimberly E Vander Woude
(74) *Attorney, Agent, or Firm* — Wilson Sonsini Goodrich & Rosati

(57) ABSTRACT

A method for assessing tissue remodeling risk is provided. The method comprises (a) obtaining a plurality of images of a target region of a subject's skin, wherein the plurality of images comprises (1) a set of visible light images and (2) a set of fluorescent images; (b) processing the plurality of images to determine an optimal image pair for the target region, wherein the optimal image pair comprises: (i) a first visible light image selected from (1), and (ii) a first fluorescent image selected from (2); (c) generating an assessment of the target region based at least on the optimal image pair; and (d) displaying on a graphical user interface the assessment, the optimal image pair, and a schematic showing a location of the target region on the subject's body, wherein the assessment is indicative of a probability of tissue remodeling at the target region.

18 Claims, 22 Drawing Sheets

Related U.S. Application Data

(60) Provisional application No. 63/132,979, filed on Dec. 31, 2020.

(51) Int. Cl.
*G16H 50/30* (2018.01)
*A61B 34/10* (2016.01)
*A61B 90/00* (2016.01)

(52) U.S. Cl.
CPC ............ *A61B 5/0077* (2013.01); *A61B 5/444* (2013.01); *A61B 5/7275* (2013.01); *G16H 50/30* (2018.01); *A61B 2034/107* (2016.02); *A61B 2090/373* (2016.02)

(58) Field of Classification Search
CPC ........ A61B 2034/107; A61B 2090/373; A61B 5/0059; A61B 5/7425; G16H 50/30
USPC .......................................................... 705/2, 3
See application file for complete search history.

(56) References Cited

U.S. PATENT DOCUMENTS

| | | | |
|---|---|---|---|
| 4,786,813 | A | 11/1988 | Svanberg et al. |
| 4,870,484 | A | 9/1989 | Sonehara |
| 5,094,531 | A | 3/1992 | Garner et al. |
| 5,432,876 | A | 7/1995 | Appeldorn et al. |
| 5,536,814 | A | 7/1996 | Ruoslahti et al. |
| 5,650,135 | A | 7/1997 | Contag et al. |
| 5,686,300 | A | 11/1997 | Berndt |
| 5,699,798 | A | 12/1997 | Hochman et al. |
| 5,717,959 | A | 2/1998 | Tokunaga |
| 5,759,996 | A | 6/1998 | Cheng et al. |
| 5,798,805 | A | 8/1998 | Ooi et al. |
| 5,836,872 | A | 11/1998 | Kenet et al. |
| 5,981,478 | A | 11/1999 | Ruoslahti et al. |
| 6,091,983 | A | 7/2000 | Alfano et al. |
| 6,284,223 | B1 | 9/2001 | Luiken |
| 6,512,236 | B2 | 1/2003 | Seville |
| 6,627,446 | B1 | 9/2003 | Roach et al. |
| 6,748,259 | B1 | 6/2004 | Benaron et al. |
| 6,748,529 | B2 | 6/2004 | Smith |
| 6,863,650 | B1 | 3/2005 | Irion |
| 7,139,598 | B2 | 11/2006 | Hull et al. |
| 7,365,844 | B2 | 4/2008 | Richards-Kortum et al. |
| 7,371,364 | B2 | 5/2008 | Li et al. |
| 7,561,287 | B1 | 7/2009 | Antonacci et al. |
| 7,564,550 | B2 | 7/2009 | Yaroslavsky et al. |
| 7,720,532 | B2 | 5/2010 | Hashimshony et al. |
| 7,842,466 | B1 | 11/2010 | Kim et al. |
| 8,642,009 | B2 | 2/2014 | Shachaf et al. |
| 10,165,976 | B2 | 1/2019 | Shachaf et al. |
| 10,531,824 | B2 | 1/2020 | Shachaf et al. |
| 11,185,278 | B2 | 11/2021 | Shachaf et al. |
| 2002/0058864 | A1 | 5/2002 | Mansfield et al. |
| 2004/0057094 | A1 | 3/2004 | Olszak et al. |
| 2004/0220100 | A1 | 11/2004 | Waugh et al. |
| 2005/0026181 | A1 | 2/2005 | Davis et al. |
| 2005/0059034 | A1 | 3/2005 | Tyler et al. |
| 2005/0118640 | A1 | 6/2005 | Kureshy et al. |
| 2005/0136177 | A1 | 6/2005 | Hesse |
| 2005/0265606 | A1 | 12/2005 | Nakamura |
| 2006/0127946 | A1 | 6/2006 | Montagu et al. |
| 2006/0148028 | A1 | 7/2006 | Noda et al. |
| 2006/0227325 | A1 | 10/2006 | Rulison et al. |
| 2007/0020181 | A1 | 1/2007 | Workman et al. |
| 2007/0255169 | A1 | 11/2007 | Hashimshony et al. |
| 2008/0032328 | A1 | 2/2008 | Cline et al. |
| 2008/0267882 | A1 | 10/2008 | Chen et al. |
| 2008/0272312 | A1 | 11/2008 | Tuschel |
| 2008/0317325 | A1 | 12/2008 | Ortyn et al. |
| 2009/0130650 | A1 | 5/2009 | Tan et al. |
| 2009/0253991 | A1 | 10/2009 | Balas et al. |
| 2009/0273447 | A1 | 11/2009 | Selker et al. |
| 2009/0297450 | A1 | 12/2009 | Ruoslahti et al. |
| 2010/0042004 | A1 | 2/2010 | Dhawan |
| 2010/0121156 | A1 | 5/2010 | Yoo |
| 2010/0185064 | A1* | 7/2010 | Bandic .................. A61B 5/444 600/306 |
| 2010/0204064 | A1 | 8/2010 | Cho |
| 2010/0214430 | A1 | 8/2010 | De Boer et al. |
| 2010/0322862 | A1 | 12/2010 | Ruoslahti et al. |
| 2011/0009163 | A1 | 1/2011 | Fletcher et al. |
| 2011/0021908 | A1 | 1/2011 | Lee et al. |
| 2011/0059016 | A1 | 3/2011 | Ramanujam et al. |
| 2011/0064658 | A1 | 3/2011 | Scherz et al. |
| 2011/0065899 | A1 | 3/2011 | Kon et al. |
| 2011/0085974 | A1 | 4/2011 | Chung et al. |
| 2011/0104075 | A1 | 5/2011 | Dmochowski et al. |
| 2011/0117025 | A1 | 5/2011 | Dacosta et al. |
| 2011/0117028 | A1 | 5/2011 | Zharov |
| 2011/0165075 | A1 | 7/2011 | Rajopadhye et al. |
| 2011/0217207 | A1 | 9/2011 | Fujimoto et al. |
| 2011/0264209 | A1 | 10/2011 | Wiechmann et al. |
| 2011/0278554 | A1 | 11/2011 | Ma et al. |
| 2011/0294543 | A1 | 12/2011 | Lapstun et al. |
| 2012/0068855 | A1 | 3/2012 | Matsumura et al. |
| 2012/0083005 | A1 | 4/2012 | Malecki et al. |
| 2012/0083761 | A1 | 4/2012 | Malecki et al. |
| 2012/0093730 | A1 | 4/2012 | Malecki et al. |
| 2012/0123205 | A1 | 5/2012 | Nie et al. |
| 2012/0330284 | A1 | 12/2012 | Hyde et al. |
| 2013/0100272 | A1 | 4/2013 | Price et al. |
| 2014/0348410 | A1* | 11/2014 | Grunkin ................ G06T 7/0012 382/133 |
| 2014/0350395 | A1* | 11/2014 | Shachaf ............... H04N 23/673 600/431 |
| 2017/0049380 | A1 | 2/2017 | Shachaf et al. |
| 2019/0113423 | A1 | 4/2019 | Goodman et al. |
| 2019/0307391 | A1* | 10/2019 | Shachaf .................... G06T 7/74 |
| 2020/0049599 | A1 | 2/2020 | Alexander et al. |
| 2020/0121245 | A1* | 4/2020 | Barclay ................ A61B 5/7275 |

FOREIGN PATENT DOCUMENTS

| | | | |
|---|---|---|---|
| CN | 1799067 | A | 7/2006 |
| CN | 102099671 | A | 6/2011 |
| CN | 103168242 | A | 6/2013 |
| CN | 110088804 | A | 8/2019 |
| EP | 0927045 | B1 | 12/2005 |
| JP | 2003513735 | A | 4/2003 |
| JP | 2011133366 | A | 7/2011 |
| JP | 2011521237 | A | 7/2011 |
| JP | 2015505051 | A | 2/2015 |
| JP | 2019521829 | A | 8/2019 |
| WO | WO-9013091 | A1 | 11/1990 |
| WO | WO-9710507 | A1 | 3/1997 |
| WO | WO-9809155 | A1 | 3/1998 |
| WO | WO-0125399 | A2 | 4/2001 |
| WO | WO-0125410 | A2 | 4/2001 |
| WO | WO-02080771 | A1 | 10/2002 |
| WO | WO-03067230 | A1 | 8/2003 |
| WO | WO-2005020794 | A2 | 3/2005 |
| WO | WO-2005034926 | A2 | 4/2005 |
| WO | WO-2005034926 | A3 | 6/2005 |
| WO | WO-2005072622 | A1 | 8/2005 |
| WO | WO-2005077065 | A2 | 8/2005 |
| WO | WO-2006083986 | A2 | 8/2006 |
| WO | WO-2006083986 | A3 | 11/2006 |
| WO | WO-2006083986 | A9 | 1/2007 |
| WO | WO-2011072401 | A1 | 6/2011 |
| WO | WO-2011112559 | A2 | 9/2011 |
| WO | WO-2018087984 | A1 | 5/2018 |
| WO | WO-2022147090 | A1 | 7/2022 |

OTHER PUBLICATIONS

Balch, Charles M., et al. Final Version of the American Joint Committee on Cancer Staging System for Cutaneous Melanoma. Journal of Clinical Oncology, vol. 19, 3635-3648 (2001).

(56) References Cited

OTHER PUBLICATIONS

Breslow, Alexander. Thickness, Cross-Sectional Areas and Depth of Invasion in the Prognosis of Cutaneous Melanoma. Annals of Surgery, vol. 172, 902-908 (1970).
Bussau, L.J., et al. Fibre optic confocal imaging (FOCI) of keratinocytes, blood vessels and nerves in hairless mouse skin in vivo. Journal of Anatomy, vol. 192, 187-194 (1998).
Cai, Weibo, et al. Multimodality tumor imaging targeting integrin $\alpha v\beta 3$. BioTechniques, vol. 39, 14-25 (2005).
Carmeliet, Peter, et al. Angiogenesis in cancer and other diseases. Nature, vol. 407, 249-257 (2000).
Chatziioannou, Arlon F. Instrumentation for Molecular Imaging in Preclinical Research: Micro-PET and Micro-SPECT. Proceedings of the American Thoracic Society, vol. 2, 533-536 (2005).
Danhier, Fabienne, et al. RGD-Based Strategies to Target Alpha(v) Beta(3) Integrin in Cancer Therapy and Diagnosis. Molecular Pharmaceutics, vol. 9, 2961-2973 (2012).
Ellis, Lee M., et al. Synopsis of Angiogenesis Inhibitors in Oncology. Oncology, vol. 16, 14-22 (2002).
EP 21916399.5 Extended European Search Report dated May 7, 2024.
Folkman, J., et al. Tumor Angiogenesis: Effect on Tumor Growth and Immunity. Fundamental Aspects of Neoplasia, 401-412 (1975).
Folkman, Judah. Tumor Angiogenesis: Therapeutic Implications. The New England Journal of Medicine, vol. 285, 1182-1186 (1971).
Gaertner, F.C., et al. Radiolabelled RGD peptides for imaging and therapy. European Journal of Nuclear Medicine and Molecular Imaging, vol. 39, S126-S138 (2012).
Haubner, Roland, et al. Noninvasive Imaging of alpha(v)beta(3) Integrin Expression Using 18F-labeled RGD-containing Glycopeptide and Positron Emission Tomography. American Association for Cancer Research, vol. 61, 1781-1785 (2001).
Hauser, Peter C., et al. A solid-state instrument for fluorescence chemical sensors using a blue light-emitting diode of high intensity. Measurement Science and Technology, vol. 6, 1081-1085 (1995).
Heasley, Diane D., et al. Pathology of Malignant Melanoma, The Surgical Clinics of North America, vol. 76, 1223-1255 (1996).
Kollias, Nikiforos, et al. Optical Non-Invasive Approaches to Diagnosis of Skin Diseases. The Journal of Investigative Dermatology, vol. 7, 64-75 (2002).
Lakowicz, Joseph R. Instrumentation for Fluorescence Spectroscopy In Principles of Fluorescence Spectroscopy. 3rd Edition, 19-27 and 32-36 (2006).
Lange, Norbert. Controlled Drug Delivery in Photodynamic Therapy and Fluorescence-Based Diagnosis of Cancer. Handbook of Biomedical Fluorescence, Chapter 16, 563-635 (2003).
Matsumoto, Keiichi, et al. Performance Characteristics of a New 3-Dimensional Continuous-Emission and Spiral-Transmission High-Sensitivity and High-Resolution PET Camera Evaluated with the NEMA NU 2-2001 Standard. Journal of Nuclear Medicine, vol. 47, 83-90 (2006).
PCT/US2021/065470 International Search Report and Written Opinion dated Apr. 1, 2022.
Richter, A., et al. Comparison of Fluorescent Tag DNA Labeling Methods Used for Expression Analysis by DNA Microarrays. BioTechniques, vol. 33, 620-628 (2002).
Rosenthal, Eben L., et al. Use of fluorescent labeled anti-epidermal growth factor receptor antibody to image head and neck squamous cell carcinoma xenografts. Molecular Cancer Therapeutics, vol. 6, 1230-1238 (2007).
Schmieder, Anne H., et al. Molecular MR Imaging of Melanoma Angiogenesis with Alpha(v)Beta(3)-Targeted Paramagnetic Nanoparticles. Magnetic Resonance in Medicine, vol. 53, 621-627 (2005).
Srivastava, Anurag, et al. Neovascularization in Human Cutaneous Melanoma: A Quantitative Morphological and Doppler Ultrasound Study. European Journal of Cancer & Clinical Oncology, vol. 22, 1205-1209 (1986).
Suihko, Christian, et al. Fluorescence fibre-optic confocal microscopy of skin in vivo: microscope and fluorophores. Skin Research and Technology, vol. 11, 254-67 (2005).
Swindle, Lucinda D., et al. View of Normal Human Skin In Vivo as Observed Using Fluorescent Fiber-Optic Confocal Microscopic Imaging. The Journal of Investigative Dermatology, vol. 121, 706-712 (2003).
Van Dam, Gooitzen M., et al. Intraoperative tumor-specific fluorescence imaging in ovarian cancer by folate receptor-$\alpha$ targeting: first in-human results. Nature Medicine, vol. 17, 1315-1319 (2011).
CN202180094945.2 Office Action with Search Report dated Mar. 19, 2026.
EP21916399.5 Communication Pursuant To Article 94(3) dated Mar. 12, 2026.

* cited by examiner

SYSTEMS AND METHODS FOR ASSESSING TISSUE REMODELING

CROSS-REFERENCE

This application is a continuation of PCT Application No. PCT/US21/65470, filed Dec. 29, 2021, which claims the benefit of U.S. Provisional Application No. 63/132,979 filed Dec. 31, 2020, the entire content of which are incorporated herein by reference in their entirety.

BACKGROUND

Cancer is a leading cause of death worldwide. Skin cancers are among the most common cancers, with melanoma being the most aggressive form of skin cancer. Current techniques for diagnosing melanoma include observation of changes in the visual appearance (size, shape, color) of an existing mole or the appearance of a new mole, determination of medical history risk factors (age, family history, etc.), biopsy, and histological analysis. The decision whether to biopsy a mole depends largely on the surface appearance of the mole. However, changes in the visible appearance of a mole is not always conclusive of the presence of melanoma in a mole as sub-surface characteristics are often missed using standard techniques. For example, one such characteristic is the presence of neovascularization and tissue remodeling. As the tumor grows, it sends out signals to prepare the local environment for expanded tumor growth (e.g., tissue remodeling) and increased nutrient supply (e.g., neoangiogenesis). Such signals can be mediated by growth factors, cytokines, and other proteins released from the tumor cells and/or from the tumor microenvironment during expansion. These processes can be investigated by testing the tissue surrounding the tumor (e.g., the macro environment) and can be used in conjunction with standard diagnostic techniques to inform diagnosis and/or treatment procedures. However, most methods for such investigation require biopsy and histological analysis which is invasive, takes significant time, and is less than ideal.

SUMMARY

It would therefore be desirable to provide systems and methods for improved visual, pre-biopsy assessment of tissue remodeling risk in a quick and easy-to-use format to allow a user to visually compare and evaluate the probability of tissue remodeling in clinically suspicious lesions. Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein.

The present disclosure generally relates to medical devices and methods and more particularly relates to methods and apparatus for assessing tissue remodeling in the skin.

In a first aspect, a method for assessing tissue remodeling risk is provided. The method comprises (a) obtaining a plurality of images of a target region of a subject's skin, wherein the plurality of images comprises (1) a set of visible light images and (2) a set of fluorescent images; (b) processing the plurality of images to determine an optimal image pair for the target region, wherein the optimal image pair comprises: (i) a first visible light image selected from (1), and (ii) a first fluorescent image selected from (2); (c) generating an assessment of the target region based at least on the optimal image pair; and (d) displaying on a graphical user interface the assessment, the optimal image pair, and a schematic showing a location of the target region on the subject's body, wherein the assessment is indicative of a probability of tissue remodeling at the target region.

In some embodiments, the target region may comprise a mole on the subject's skin. In some embodiments, the first visible light image and the first fluorescent image may be selected to be complementary or matching with each other. Alternatively, or in combination, the first visible light image may comprise a first set of visual characteristics, and the first fluorescent image may comprise a second set of visual characteristics. At least a portion of the second set of visual characteristics may not be visible in the first set of visual characteristics and at least a portion of the first set of visual characteristics may not be visible in the second set of visual characteristics. In some embodiments, the first set of visual characteristics may be generated by using visible or white light to image the target region. In some embodiments, the second set of visual characteristics may be generated by using infrared light to image the target region. In some embodiments, the first set of visual characteristics may be associated with the mole and the exposed skin of the subject. In some embodiments, the second set of visual characteristics may be associated with underlying tissue beneath the skin and surrounding the mole in the macroenvironment (i.e., the tissue surrounding, but not including, the mole).

In some embodiments, the optimal image pair may be determined from the plurality of images based at least on one or more of the following: focus quality, contrast, clarity, brightness, color, or resolution.

In some embodiments, the optimal image pair may be determined from the plurality of images based at least on: (1) a position of the target region within each of the visible light images and each of the fluorescent images, (2) a degree of similarity or correlation between each of the visible light images with each of the fluorescent images, and/or (3) a focus quality of each of the visible light image and each of the fluorescent images.

In some embodiments, processing the plurality of images may comprise at least one of the following: size filtering, normalization, standardization, reducing noise, elimination of imaging artifacts, background subtraction, cropping, magnification, resizing, repositioning, brightness adjustment, contrast adjustment, or object segmentation.

In some embodiments, the optimal image pair may be a first optimal image pair. In some embodiments, the method may comprise, after (b) and prior to (c): displaying an option on the graphical user interface to a user, wherein the option may permit the user to accept or reject the first optimal image pair; and receiving an input from the user in response to the option displayed on the graphical user interface. In some embodiments, the method may further comprise processing the plurality of images to determine a second optimal image pair for the target region when the input is indicative of the user rejecting the first optimal image pair, wherein the second optimal image pair is different from the first optimal image pair. In some embodiments, the second optimal image pair and the first optimal image pair may not share any common images. Alternatively, the second optimal image pair and the first optimal image pair may share a common image. In some embodiments, the common image may comprise either the first visible light image or the first fluorescent image. In some embodiments, the method may further comprise redisplaying the option on the graphical user interface to a user, wherein the option may permit the user to accept or reject the second optimal image pair; and receiving another input from the user in response to the option displayed on the graphical user interface. In some embodiments, (c) may comprise generating the assessment for the target region based at least on the second optimal image pair instead of the first optimal image pair, when another input is indicative of the user accepting the second optimal image pair. Alternatively, or in combination, the method may comprise continuing with (c) and (d) when the input is indicative of the user accepting the first optimal image pair. In some embodiments, the method may comprise processing the plurality of images to determine a plurality of other optimal image pairs for the target region when the input is indicative of the user rejecting the first optimal image pair; and displaying the plurality of other optimal image pairs on the graphical user interface. The plurality of other optimal image pairs may be sequentially displayed on the graphical user interface to the user.

In some embodiments, (b) may further comprise processing the plurality of images to determine a plurality of image pairs, wherein the plurality of image pairs may comprise the optimal image pair. In some embodiments, the optimal image pair may be annotated to visually distinguish over the other image pairs. In some embodiments, the optimal image pair may be annotated by placing a predefined border around the optimal image pair.

In some embodiments, (b) may further comprise automatically detecting the mole within the target region, and generating a graphical boundary or outline around the mole. In some embodiments, the graphical boundary or outline may be automatically generated to follow a shape or contour of the mole. Alternatively, or in combination, the graphical boundary or outline may be adjustable or created by a user via the graphical user interface.

In some embodiments, the assessment may comprise an aggregate score for the optimal image pair. The aggregate score may be a composite of two or more discrete scores. In some embodiments, the two or more discrete scores may comprise (1) a score for the first visible light image and (2) a score for the first fluorescent image. In some embodiments, the composite of the two or more discrete scores may be weighted equally such that the score for the first visible light image and the score for the first fluorescent image are both given a same weight. In some embodiments, the composite of the two or more discrete scores may be weighted differently such that the score for the first visible light image and the score for the first fluorescent image are given different weights. For example, the score for the first fluorescent image may be given a higher weight than the score for the first visible light image. Alternatively, the score for the first fluorescent image may be given a lower weight than the score for the first visible light image. In some embodiments, the aggregate score may lie within a value range. In some embodiments, the two or more discrete scores may lie within a value range. In some embodiments, the score for the first visible light image and the score for the first fluorescent image may be based on a standardized value range.

In some embodiments, the probability of tissue remodeling may be associated with a probability of development of melanoma in the mole. In some embodiments, the assessment may be useable to determine a clinical diagnosis or course of action based on the probability of development of melanoma in the mole. In some embodiments, the method may comprise generating one or more notifications on the graphical user interface when the probability of tissue remodeling at the target region or the probability of development of melanoma is greater than one or more threshold values.

In some embodiments, the assessment may be generated based at least on: (1) a first set of metrics associated with the first set of visual characteristics in the first visible light image and (2) a second set of metrics associated with the second set of visual characteristics in the first fluorescent image. In some embodiments, the first set of metrics may comprise one or more of the following: size, shape, volume, color, or surface texture of the mole and its surrounding area. In some embodiments, the second set of metrics may comprise one or more of the following: size, shape, area or extent of tissue remodeling, pixel intensity, fluorescence intensity, patterns or texture in the target region beneath the subject's skin and surrounding the mole. In some embodiments, the method may further comprise segmenting the first visible light image or the first fluorescent image to generate the first set of metrics or the second set of metrics, respectively. Segmenting the first fluorescent image may comprise segmenting the first fluorescent image into a plurality of zones surrounding the target region. In some embodiments, the method may further comprise dividing the plurality of zones into a plurality of sub-regions.

In some embodiments, the first visible light image and the first fluorescent image may be adjusted and aligned to a set of coordinates within the optimal image pair. In some embodiments, the first visible light image and the first fluorescent image may be adjusted and aligned by rotating, translating, cropping, magnifying, and/or de-magnifying at least one of the first visible light image and the first fluorescent image. In some embodiments, the first visible light image and the first fluorescent image may be adjusted and aligned using one or more fiducial markers present in both the first visible light image and the first fluorescent image. The one or more fiducial markers may be annotated on the first visible light image and the first fluorescent image. Alternatively, or in combination, the one or more fiducial markers may be visible in both the first visible light image and the first fluorescent image. Alternatively, or in combination, the one or more fiducial markers may comprise one or more alphanumeric characters. Alternatively, or in combination, the one or more fiducial markers may comprise a line, edge, dot or a two-dimensional shape. In some embodiments, the one or more fiducial markers may be provided at one or more predefined locations within the target region. Alternatively, or in combination, the one or more fiducial markers may be provided at a predefined distance and/or orientation relative to a location of the mole.

In some embodiments, the method may comprise comparing the optimal image pair to one or more reference images. In some embodiments, the one or more reference images may comprise a reference image pair. In some embodiments, the reference image pair may comprise (1) a visible light reference image that is not from the set of visible light images and (2) a fluorescent reference image that is not from the set of fluorescent images. In some embodiments, the optimal image pair may comprise fiducials, and wherein the reference image pair does not comprise fiducials. In some embodiments, the optimal image pair may comprise a first set of fiducials that are located at a predefined location and/or orientation relative to the mole, and the reference image pair may comprise a set of fiducials that are located near a boundary of each reference image within the reference image pair.

In some embodiments, the graphical user interface may be configured to permit a user to toggle or switch between the first visible light image or the first fluorescent image within the optimal image pair.

In some embodiments, the first visible light image may focus on the mole on the subject's skin, and the first fluorescent image may focus on an area surrounding the mole beneath the subject's skin. Optionally, the area may be at least 1.5 times greater than a size of the mole.

In some embodiments, obtaining the plurality of images of the target region may comprise autofocusing an integrated imaging system using structured light and capturing the plurality of images with the integrated imaging system after autofocusing.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The present disclosure is described in relation to deployment of systems, devices, or methods for assessing tissue remodeling in the skin of a patient. However, one of skill in the art will appreciate that this is not intended to be limiting and the devices, systems, and methods disclosed herein may be used in other anatomical areas and/or to assess other aspects of a tissue. For example, tissue cavities or surfaces such as the mouth, colon, digestive system, cervix, bladder, lung, lymph nodes, etc. The devices, systems, and methods disclosed herein may be used to image surface and/or non-surface tissues as desired by one of ordinary skill in the art.

Figure 1:
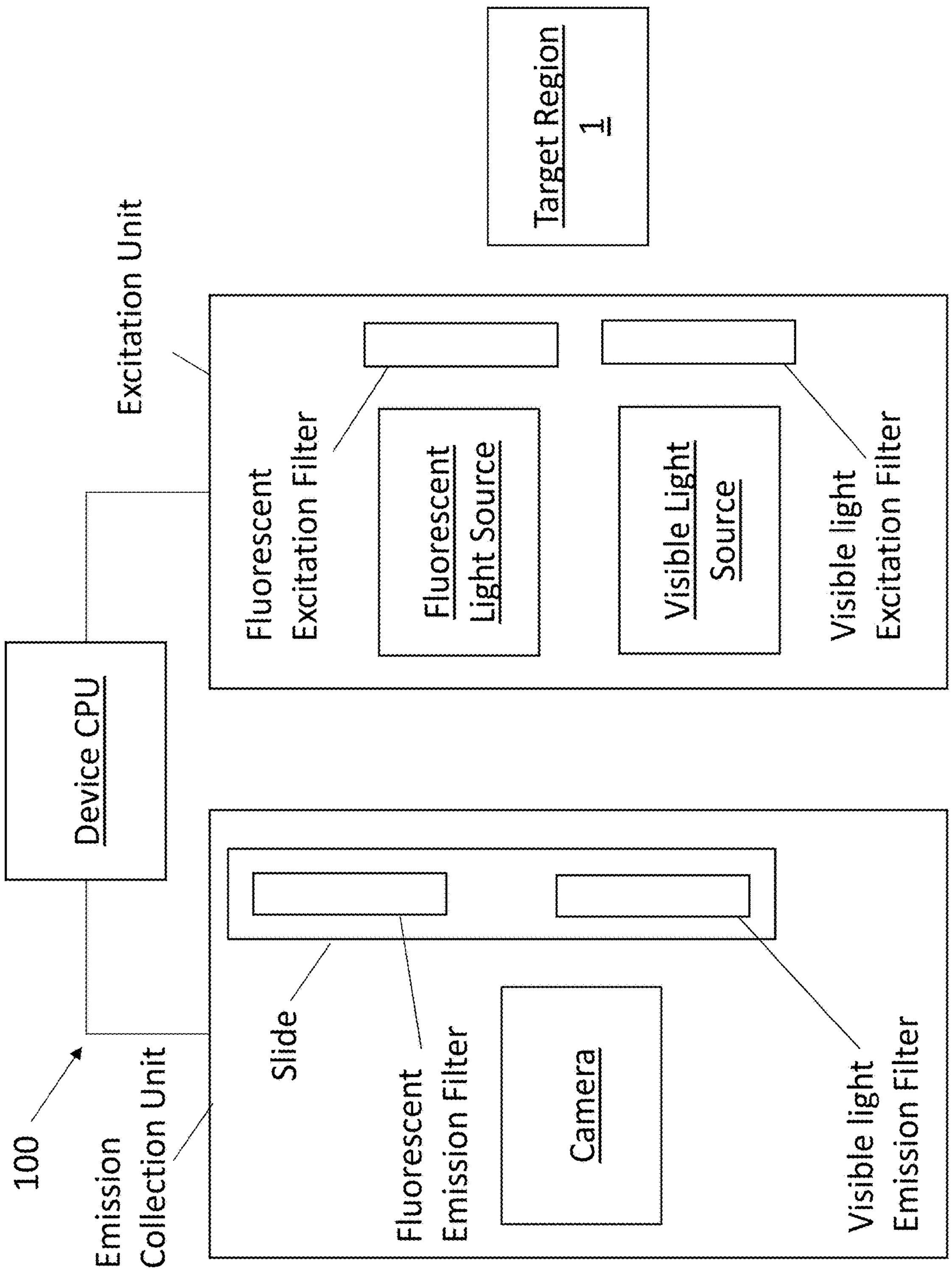
FIG. 1 shows a schematic of an exemplary system for obtaining at least a pair of images, in accordance with embodiments.
Figure 2:
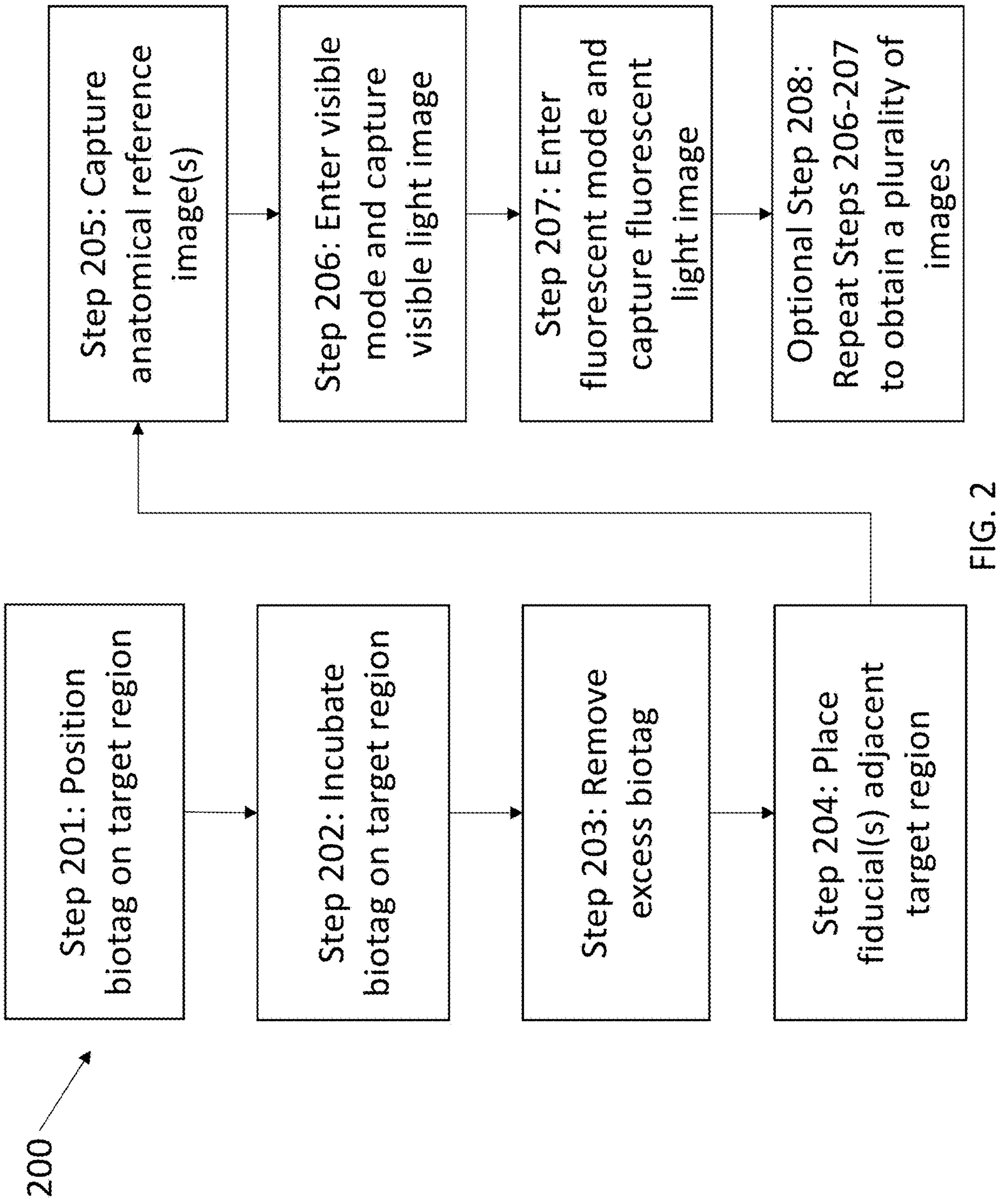
FIG. 2 shows a flowchart of a method of obtaining at least a pair of images, in accordance with embodiments.

FIGS. 1 and 2 show an exemplary system, device, and method for obtaining a pair of images from a target region. However, it will be apparent to one of ordinary skill in the art that this is not intended to be limiting and that the image analysis systems and methods disclosed herein may be used in conjunction with any suitable pair of images obtained from a target region, regardless of what device, system, or method was for their acquisition. The choice of image acquisition device may be determined based on the accessibility of the tissue location, facilities and/or technologies available at the point of care, operational cost, etc.

FIG. 1 shows a schematic of an exemplary system 100 for obtaining at least a pair of images from a target region 1. The system 100 may comprise an excitation unit and an emission collection unit operably coupled to one another by a processor. The system 100 may comprise a processor configured to operate the components of the emission collection unit and the excitation unit. The excitation collection unit may comprise a fluorescent light source and a visible light source. The visible light source may be a white light source, for example a white LED. The fluorescent light source may, for example, comprise an infrared LED. One or more excitation filters may be coupled to the light sources in order to refine the excitation light being directed towards the target region 1. Light may be emitted by the light sources in response to an input from a user (e.g., selecting a light mode and pressing a capture button) and directed to the target region 1. Light may be reflected, refracted, and/or emitted from the target region 1 back towards the emission collection unit. The emission collection unit may comprise a camera or other image device (e.g., PMT, CCD, etc.). One or more emission filters may be disposed in the light path between the target region 1 and the camera in order to filter incoming emission light. For example, a slide may house a fluorescent emission filter and a visible light emission filter. The fluorescent emission filter may be specific to a wavelength or range of wavelengths emitted by the target region 1 when excited by the fluorescent light source. In some embodiments, the visible light emission filter may be a polarizing filter and a second polarizing filter (e.g., a visible light excitation filter), rotated 90 degrees relative to the visible light emission filter, may be disposed in the light path between the visible light source and the target region 1. The use of two polarizing filters may remove speckles (i.e., reflections from oil on the skin) from the target region 1. The system 100 may be used to collect at least a first pair of images of the target region 1 comprising a first visible light image and a first fluorescent light image.

Note that the elements shown in FIG. 1 are not to scale and the arrangement of the elements as shown is purely exemplary. The number of light sources may vary. Light directing elements such as mirrors, prisms, light-pipes, fiber optics, and/or splitters may be used to direct the light. Not all elements are required in all embodiments.

The system 100 may include one or more elements of the systems described in US2017/0049380 or US2019/0307391, the entire disclosures of which are incorporated herein for all purposes.

The system 100 may be an integrated imaging system including a self-contained camera or non-contained camera with the following components: case, power supply, lens, image sensor, image storage memory, user controls, user display, internal control electronics including stored instructions for an embedded processor, and internal image processing logic including stored instructions for an embedded processor. A consumer or professional digital single-lens reflex (DSLR) camera is one non-limiting example of an integrated imaging system. The integrated imaging system may have interchangeable lenses, although this is not a requirement. The integrated imaging system may have an autofocus capability, such as a mirror-less contrast detection autofocus method or a phase detection method using a mirror and a separate sensor. The lens may have macro-focusing capability. The integrated imaging system may have removable image storage modules (e.g., SD cards) and/or have cable for communicating stored images, and/or a wireless communications port for communicating stored images. An integrated imaging system does not require connection to an external computer for operation, although such connection may be optional. An integrated imaging system is distinct from an industrial, medical, or compound imaging system where required components and/or functionality are split between two or more physical enclosures and one of the enclosures is or contains a computer.

One or more filters may be provided in the system 100. The system 100 may, for example, have two emission filters in a slide configured to move the filters respectively into the optical path of the camera. Any number of filters (e.g., 1, 2, 3, 4, 5 or more) may be provided. The filters may pass different wavelengths of electromagnetic radiation to pass through, relative to one another. The filters may be movable relative to the optical path of the camera and/or one another. The filters may move orthogonal to the optical path of the camera. Desired filters can be slid, pivoted, or rotated into place.

In some embodiments a single filter may be used, instead of two. In this single-filter configuration, the filter may have a band-reject notch at the excitation frequency, such as 660 nm, while letting both visible and emission band light pass. In this way, such a single filter may be used, without changing filters, for both visible and fluorescent emission exposures.

One or more (e.g., two) visible excitation light sources may be provided in order to achieve uniform illumination of the mole or other target area. One or more (e.g., two) fluorescent excitation light sources may be provided in order to achieve uniform illumination of the mole or other target area. Uniform illumination may be advantageous in achieving a calibrated or measurable response based on the biotag and/or the fiducials for this purpose. The fluorescent light source may be an LED, laser, fluorescent emitter, or other light source. In some embodiments, the fluorescent light source may have a sufficiently narrow band such that the fluorescent excitation filter is not necessary.

A structured light illumination component, such as a diffraction element or a mask, may be provided, which may be integrated with visible light source in order to achieve uniform white light illumination of the subject. The structured light illumination component may be an optical element that may pattern, diffuse, or spread light. For example, the structured light illumination component may comprise a diffraction element integrated with a laser light source or a mask configured to generate a line pattern on a target region when illuminated by LED light. Structured illumination may, for example, be used to identify hair. The structured illumination may also be used to determine the height and shape of the mole above the surface of the skin, and the texture of the mole.

The system 100 may have an autofocus configured to focus the camera on the target region under both visible light illumination and fluorescent illumination to ensure that the visible light image and the fluorescent image are taken at the same focal point. In some embodiments, the autofocus may be configured to focus the camera on the target region using structured light. In at least some instances, the use of structured light for autofocus may enhance the autofocus of the camera under fluorescent illumination compared to unstructured light, which may have higher fluorescent light scatter in the tissue and be inadequate in at least some instances for autofocus.

The system 100 may include a cavity for a memory card (not shown), which may include a wireless interface (not shown), a user display (not shown), and a user control (not shown). The user display can include a screen or other display that may show an image that may be captured by the integrated imaging device. A lens may be provided or attached to the system 100. The lens may be either integral to the integrated imaging device or the device is adapted to accept interchangeable lenses (such as a macro lens). An operating button may also be integrated within the system 100. Other user interface mechanisms such as touchscreens, levers, sliders, knobs or features may be used for a user to interface with or interact with the integrated imaging device.

FIG. 2 shows a flowchart of a method 200 of obtaining at least a pair of images.

At Step 201, the biotag may be positioned on the target region of the patient. The biotag may be detectably (e.g., fluorescently) labeled. The biotag may selectively bind to a targeted binding partner present in the target region of interest. Alternatively, the biotag may be absorbed, metabolized, internalized, or retained in another manner in reactive tissue of the target region. Application may be topical (e.g., with a gel, liquid, etc.), for example application to the surface of the skin using a skin penetration agent or facilitator, or may be applied by sub- or intra-dermal injection (e.g., with an array of microneedles or by electrical conductivity). The biotag formulation can comprise a solvent, and optionally blocker, skin penetrator and/or an enhancer, ion-pairing agent, co-solvent. and/or humectants and/or thickeners, alone or in various combinations.

A biotag is a specific binding partner to a targeted molecule of interest. Examples of biotags may include, without limitation, peptide, peptidomimetic, peptoid, circular peptide, etc.; a nucleic acid such as RNA, DNA, aptamer, etc.; or other organic compound. One, or a cocktail of biotags of 2, 3 4, or more different moieties may be used in the methods described herein for multiplex imaging. The biotag may be of a molecular weight small enough to effectively cross the epidermal surface, e.g. usually less than 10,000 daltons, less than 5,000 daltons, less than 2,500 daltons, less than 1,000 daltons, which penetration may be facilitated by a penetration agent. The biotag generally comprises a detectable label.

Molecules suitable as binding partners to a biotag may include, for example, cancer-associated markers present on cancer or pre-cancerous cells, or in the macroenvironment of cancerous or pre-cancerous cells, e.g. the vasculature at the site of the lesion. Specific markers of interest for this purpose include, without limitation, molecules associated with tumor vasculature, such as integrins, including integrin av, integrin a5, integrin 03, integrin 31, etc. Biotags suitable for detection of such integrins can include peptides comprising an RGD motif or mimetics thereof, as known and used in the art. See, for example, Gaertner et al. (2012) Eur J Nucl Med Mol Imaging. 39 Suppl 1:S1 26-38; Danhier et al. (2012) Mo. Pharm. 9(1 1):2961-73, herein specifically incorporated by reference. Other biotags of interest may include, without limitation, hormones, antigen binding fragments of antibodies, EGF, IGF, etc. While tumor-associated biotags are described in detail herein, it will be understood by one of ordinary skill in the art that the systems and methods described herein may be used to assess non-tumorous markers as well, particularly when the tissue to be assessed is not cancerous.

Tumor-associated antigens may include, without limitation, immunogenic sequences from MART-1, gp100 (pmel-17), tyrosinase, tyrosinase-related protein 1, tyrosinase-related protein 2, melanocyte-stimulating hormone receptor, MAGE1, MAGE2, MAGE3, MAGE12, BAGE, GAGE, NY-ESO-1, β-catenin, MUM-1, CDK4, caspase 8, KIA 0205, HLA-A2R1701, α-fetoprotein, telomerase catalytic protein, G-250, MUC-1, carcinoembryonic protein, p53, Her2/neu, TERT, PRAME, LINC00518, triosephosphate isomerase, CDC-27, LDLR-FUT, telomerase reverse transcriptase, MUC18, ICAM-1, TNF a/p, plasminogen activator (uPA), Cathepsins (B, D, H, L), PSMA, HMB-45, S-100, Melan-A (A103), (T31 1), Mitf (D5), Glypican-3, GPC3, GPNMB, MIA (melanoma inhibitory activity), MCR-1, EGF, IGF, ARPC2, FN1, RGS1, SPP1, WNT2, PECAM-1, osteopontin, glucose, MMP-s (matrix metalloproteinase family members such as MMP-1. MMP-2, MMP-9, MMP-13, MT I-MMP and others) FDG (or other metabolites), VEGF, and the like, as known in the art.

Optically visible moieties for use as a detectable marker may include fluorescent dyes, or visible-spectrum dyes, visible particles, and other visible labeling moieties. Fluorescent dyes such as fluorescein, coumarin, rhodamine, bodipy Texas red, and cyanine dyes, may be useful when sufficient excitation energy can be provided to the site to be inspected visually. Endoscopic visualization procedures may be more compatible with the use of such labels. Acceptable dyes may include FDA-approved food dyes and colors, which are non-toxic, although pharmaceutically acceptable dyes which have been approved for internal administration are preferred. Alternatively, visible particles, such as colloidal gold particles or latex particles, may be coupled to the biotag via a suitable chemical linker.

Fluorescent dyes of interest as a detectable label may include, without limitation, fluorescein (e.g., fluorescein isothiocyanate, FITC), rhodamine, indocyanine green (ICG), Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), the cyanine dyes, such as Cy3, Cy5, Cy 5.5, Alexa 542, Alexa 647, Alexa 680, Alexa 700, Bodipy 630/650, fluorescent particles, fluorescent semiconductor nanocrystals, derivatives thereof, and the like.

In some embodiments, the wavelength for emission from the label may be in the range of near ultraviolet to near infrared. Characteristics considered for label selection may include its light absorption, and a minimization of autofluorescence from the body surface to be measured. The probe may respond to florescent illumination of a specific wavelength and then emit light at a different wavelength.

In some embodiments, the wavelength for emission from the label may be in the range of the near infrared. Such labels may include, without limitation, Alexa dyes such as Alexa 647, Alexa 680, Alexa 700 and Cyanine dyes such as Cy 5, Cy5.5, and Cy7.

Other dyes may include, without limitation, any of the FDA approved dyes to use in food, e.g. FD&C Blue No. 1 E133, FD&C Blue No. E132, FD&C Green No. 3, Orange B(3), FD&C Red No. 3 E127, FD&C Red No. 40(3) E129, FD&C Yellow No. 5 E102, FD&C Yellow No. 6, D&C Black No. 2 &3, D&C Red No. 6, 7, 17, 21, 22, 27, 28, 30, 31, 33, 34, 36, 40, D&C Violet No. 2, etc.

In alternative embodiments, the biotag may be imaged by one or more modalities that may include, without limitation, optical coherence tomography, Raman spectroscopy, photo acoustic imaging, ultrasound imaging, endoscopy, and the like.

At Step 202, the biotag may be incubated on the target region. The biotag may interact with the tissue and bind to the appropriate binding partners, a process that typically takes several minutes.

At Step 203, excess, unbound biotag may be removed. In some embodiments, removal may occur via washing or wiping with water or saline solution, with or without a detergent. Depending on the application and the embodiment, excess (non-bound or non-retained) biotag can be removed after 1, 2, 3, 4, 5, 6, 7, 8, 9, 10, 11, 12, 13, 14, 15, 16, 17, 18, 18, 20 minutes or within 20-25, 25-30, 30-35, 35-40, 40-45, 50-55, 55-60 minutes, or within 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24 hours or within 1-2 days. A preferable time of biotag application is between 2 to 15 minutes and less than 2 hours. In some embodiments, excess biotag may not be removed (e.g., when the biotag is injected). Retention of the biotag in the cavity/tissue compartment may occur when the appropriate binding partner is found in the lesion macroenvironment.

At Step 204, one or more fiducial markers may be placed adjacent the target region. Prior to imaging the target region, calibration markers in the form of fiducial markers can be applied adjacent the lesion in the target region. The fiducial markers can be removably provided on the patient, drawn on the patient, affixed (removably or permanently) to the imaging device, or provided separately from the imaging device. Images may be acquired using a camera, or any of the devices, systems and methods described within this specification. The fiducial markers may allow a processor and/or user to accurately compare an image captured using a visible light source (also referred to herein as a visible light image) to an image captured using a fluorescent light source (also referred to herein as a fluorescent image). One or more fiducial marker may be visible in both the visible light spectrum and in the fluorescent emission band of the biotag, e.g., to facilitate image alignment. The markers need not appear identical in both images but they should clearly align. Because the camera may be hand-held, or because the patient may move between exposures, images taken with visible and fluorescent emission spectral light may not be naturally aligned, thus the alignment fiducial features may be particularly beneficial.

In some embodiments, the one or more fiducial markers may contain a unique barcode or other identifier for identification of the target region imaged. (Barcode generally refers to information which is unique for a specific tag, e.g.: linear barcode, 2D metric barcode.) The one or more fiducial markers can include a visual identifier. The fiducial marker may comprise a fluorescent marker or tag which comprises either the same fluorescent compound as the fluorescent marker present on the biotag, or a compound that emits light in a compatible spectra as the biotag (for example FD&C Green No. 3) so that it can be detected by the camera optics and used as a target for autofocus. In some embodiments, the fiducial may not be used for autofocusing and may instead (or additionally) be used to verify focus after the image has been uploaded into the image processing system. Compatible spectra may include, for example, a spectrum that comprises excitation light in the spectra of the excitation of the biotag, and light emission of the fiducial marker comprises a spectral emission within the spectrum of the biotag emission. In some cases, common food coloring may be used as the fluorescent compound in the fiducial marker. The fiducial marker can be applied directly to the tissue/cavity surface or on a medium that is then applied to the surface, for example a sticker or transferred from a medium to the skin, for example a temporary or permanent tattoo. In some embodiments, a plurality of fiducial markers may be applied on the exemplary sticker or tattoo.

At Step 205, anatomical reference images may be captured to mark the location of the target region.

At Step 206, the system may be set up in a visible mode and a visible light image of the target region may be captured. The visible light image may comprise a first set of visual characteristics. The first set of visual characteristics may be generated by using visible or white light to image the target region. In some embodiments, structured or patterned light may be used to image the target region, e.g., for 3-D and/or roughness analysis.

Depending on the application, images may be acquired prior to application of the biotag as well as after application.

At Step 207, the system may be transitioned into a fluorescent mode and a fluorescent image of the target region may be captured. An image (e.g., photograph) of the tissue surface may be taken using the camera and a light of the right (excitation) wavelength that activates the biotag detectable label (e.g., a fluorescent label). The fluorescent image may capture light emitted by the biotag. The fluorescent image may comprise a second set of visual characteristics. At least a portion of the first set of visual characteristics from the visible light image may be not be visible in the second set of visual characteristics from the fluorescent image (e.g., the color of the mole, etc.). The second set of visual characteristics may be generated using fluorescent light (e.g., infrared light) to image the target region. In some embodiments, the biotag may emit a fluorescent signal when excited by fluorescent light which may indicate binding of the biotag to the target marker. In some cases, presence of the target marker (and biotag fluorescence) may be associated with tissue remodeling and/or a particular disease state. In some embodiments, absence of the target marker (and biotag fluorescence) may be associated with tissue remodeling and/or a particular disease state. In some embodiments, the biotag may bind to target markers present in the macroenvironment (also referred to herein as the macro region) adjacent to the lesion of interest (e.g., mole, tumor, etc.) even when a diseased cell is not specifically in the area being imaged.

The visible light image may focus on the target region (e.g., a mole on a patient's skin) while the fluorescent image may focus on an area surrounding the target region (e.g., a macro region around the mole) beneath the surface of the target region (e.g., beneath the subject's skin). The first second of visual characteristics may be associated with a mole and the exposed skin of the subject. The second set of visual characteristics may be associated with underlying tissue beneath the skin and surrounding the mole. In some embodiments, the macro area may be at least 1.5 times larger than the size of the mole.

The same camera may be used to capture the visible light image and the fluorescent light image. While less preferred, different cameras may also be used, one for capturing the visible light image and one for capturing the fluorescent light image.

At Step 208, Steps 206 and 207 may be repeated to obtain a plurality of visible light images and a plurality of fluorescent light images. The system may be configured to alternate between visible mode and fluorescent mode in order to capture alternating visible light and fluorescent images. In some embodiments, as least two image pairs may be captured. In some embodiments, three, four, five, six, seven, eight, nine, ten, or more image pairs may be captured. Once the desired number of image pairs have been captured, the images may be transferred out of the camera to a processor for further processing and analysis (e.g., as described in FIG. 19).

Although the steps above show a method 200 of obtaining a pair of image in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to obtain a pair of images.

For example, in some embodiments Step 204 may occur before Step 201 such that the fiducial is placed adjacent the target region before the biotag is applied. Alternatively, or in combination, Step 206 and/or 207 may occur in multiple steps, some of which may be automated. In some embodiments, optional focusing steps may be added when autofocus is not used.

Figure 3:
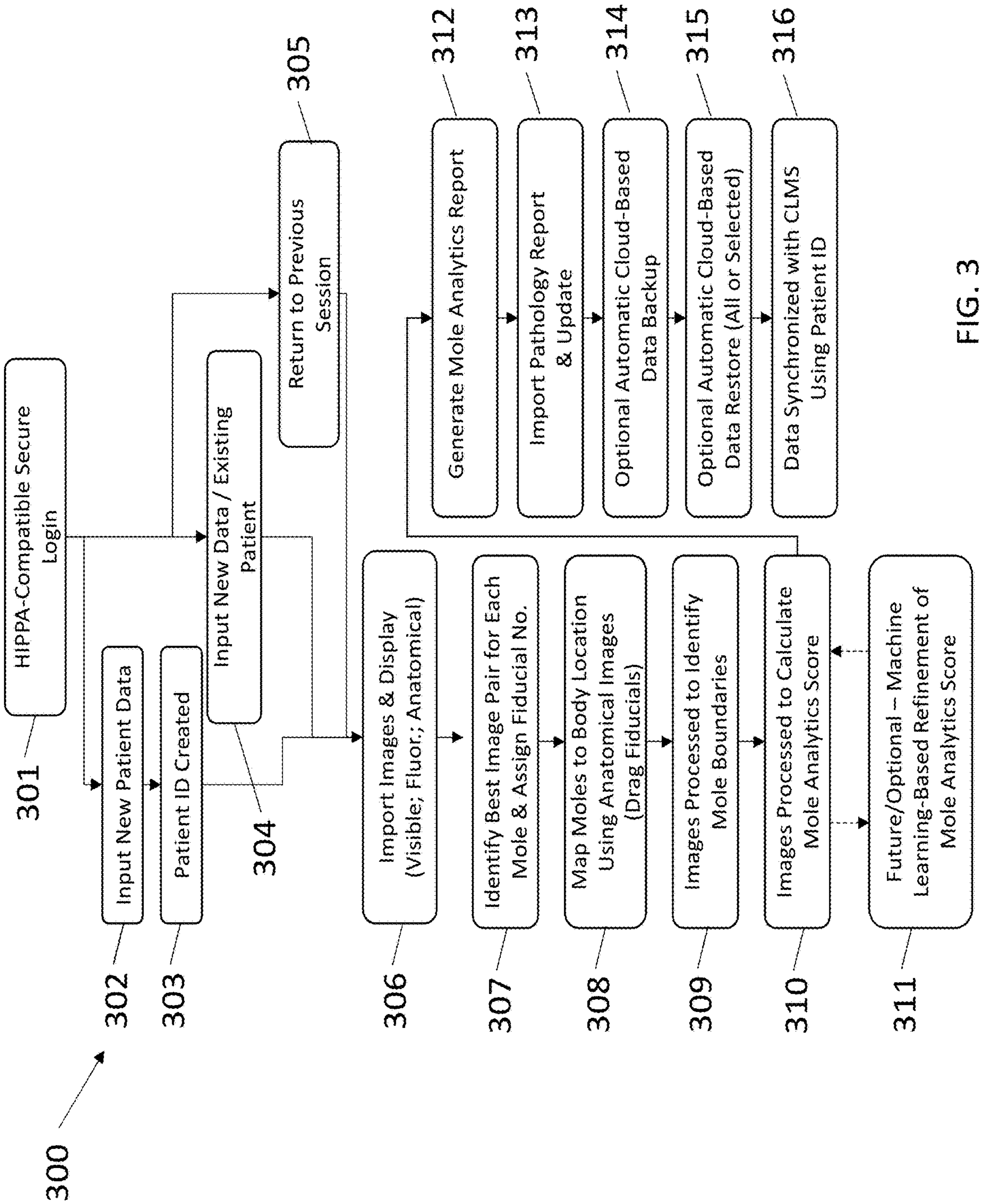
FIG. 3 shows a flowchart of a method of operating a user interface to assess a risk of tissue remodeling for a pair of images, in accordance with embodiments.

FIG. 3 shows a flowchart of a method 300 of operating a user interface to assess a risk of tissue remodeling for a pair of images.

Figure 4:
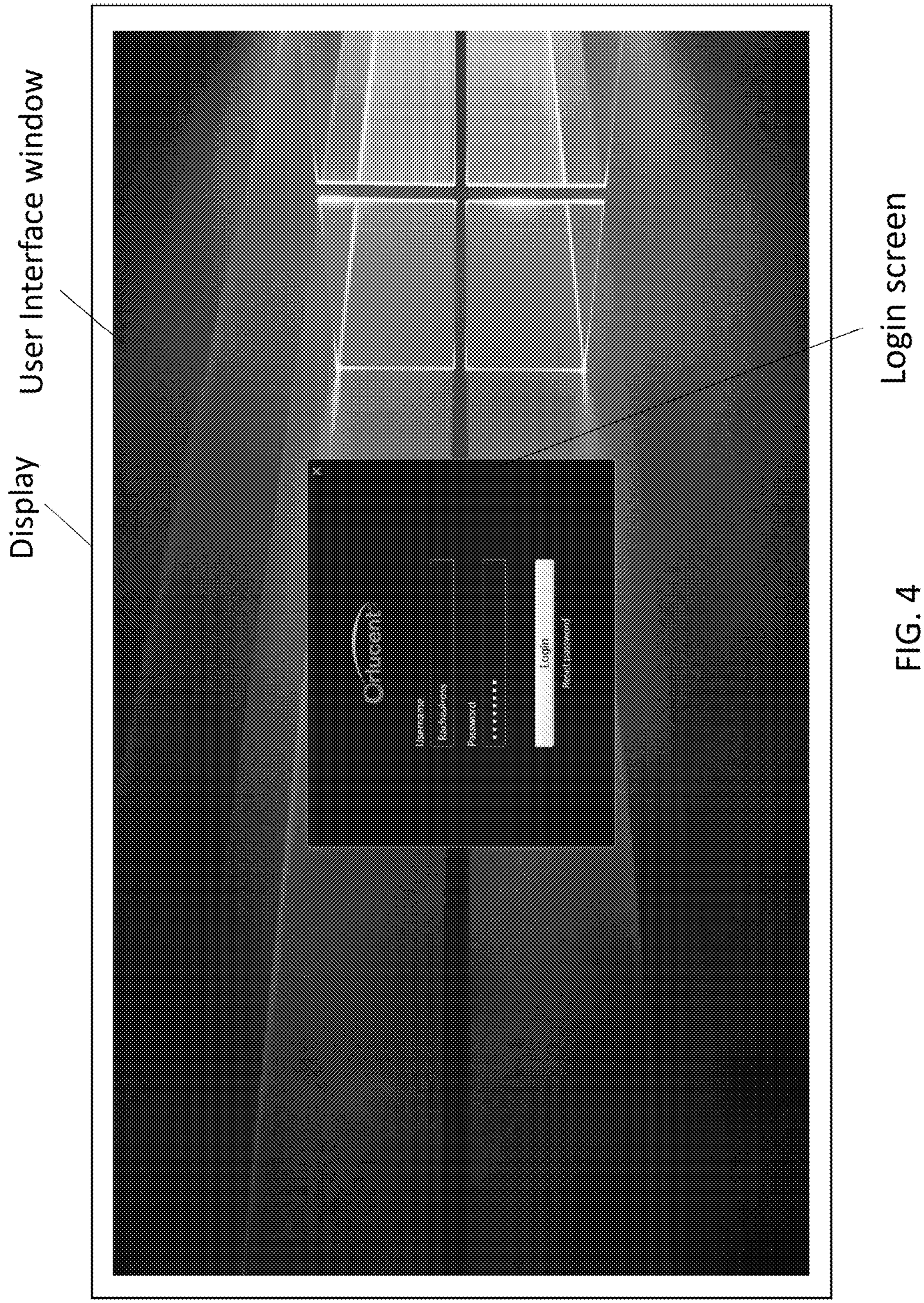
FIG. 4 shows an exemplary user interface depicting a login screen, in accordance with embodiments.

At Step 301, the user interface may display a HIPPA-compatible secure login screen (e.g., as shown in FIG. 4).

Figure 6:
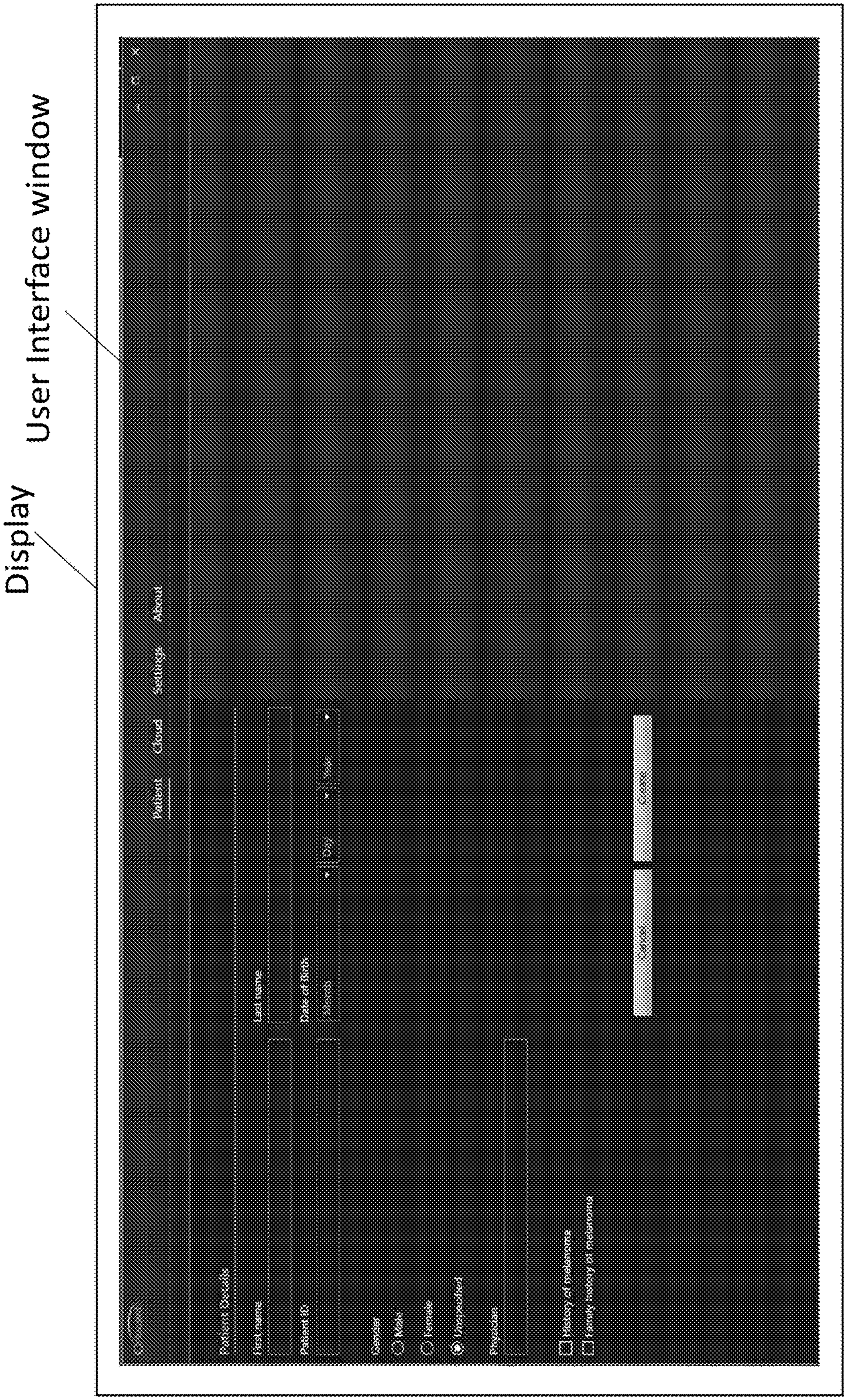
FIG. 6 shows an exemplary user interface depicting a new patient input screen, in accordance with embodiments.

At Step 302, new patient data may be input into system using the user interface (e.g., as shown in FIG. 6).

At Step 303, a unique patient identifier may be created.

At Step 304, when a patient has already been created (e.g., in a previous session using Steps 302-303), the user may bypass Steps 302-303 and input the existing user's data (e.g., using their unique patient identifier) into the system using the user interface in order to load previously-acquired data.

At Step 305, the user may optionally choose to return to a previously-saved session and bypass Steps 302-304 when the patient information is already on the system.

Figure 8:
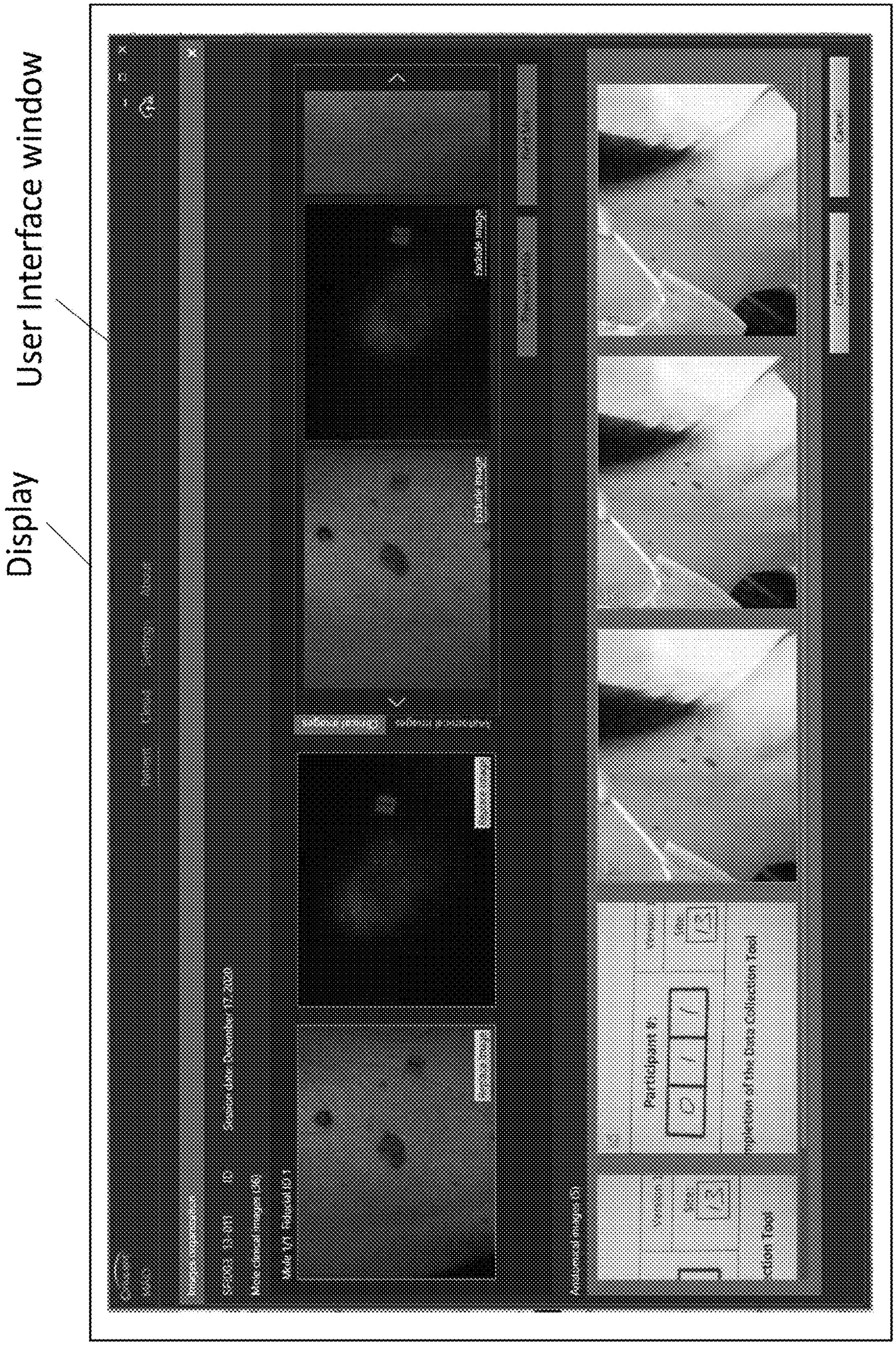
FIG. 8 shows an exemplary user interface depicting an image import screen, in accordance with embodiments.

At Step 306, a plurality of images may be imported into the system and displayed on the user interface (e.g., as shown in FIG. 8). The plurality of images may comprise a plurality of anatomical images, a plurality of visible images of a target region, and a plurality of fluorescent images of the target region. The plurality of images may be displayed to the user prior to further processing in order to enable the user to select the images to be analyzed as described herein.

At Step 307, an optimal pair of visible and fluorescent images may be identified for each mole and a unique fiducial number may be assigned to each mole. The optimal pair of visible light and fluorescent images may be identified automatically or selected by a user as described herein. In some embodiments, the optimal pair of visible and fluorescent images may be identified programmatically prior to display and fiducial number assignment.

Figure 9:
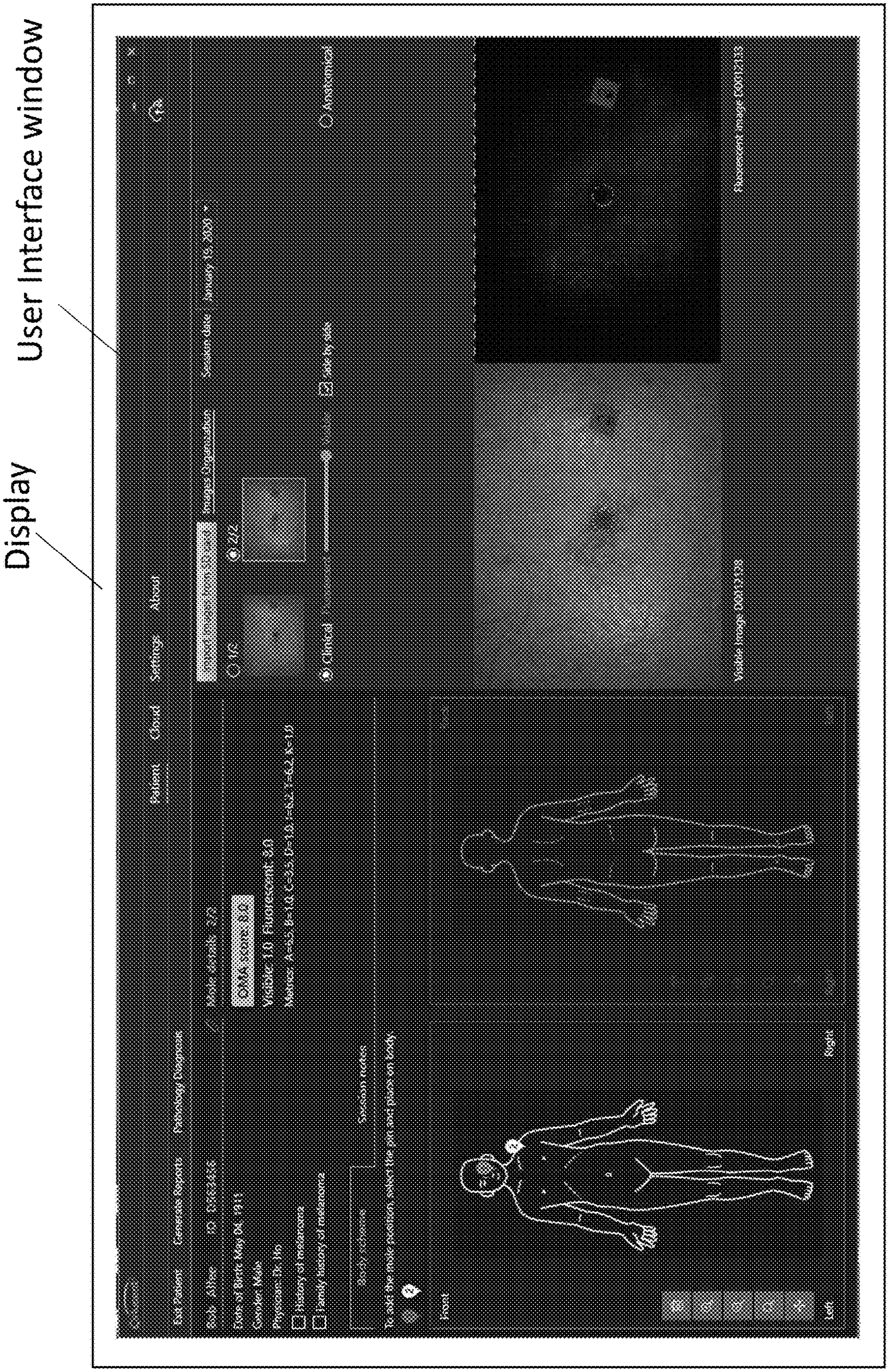
FIG. 9 shows an exemplary user interface depicting a patient card having an optimal image pair side-by-side and tissue score, in accordance with embodiments.
Figure 10:
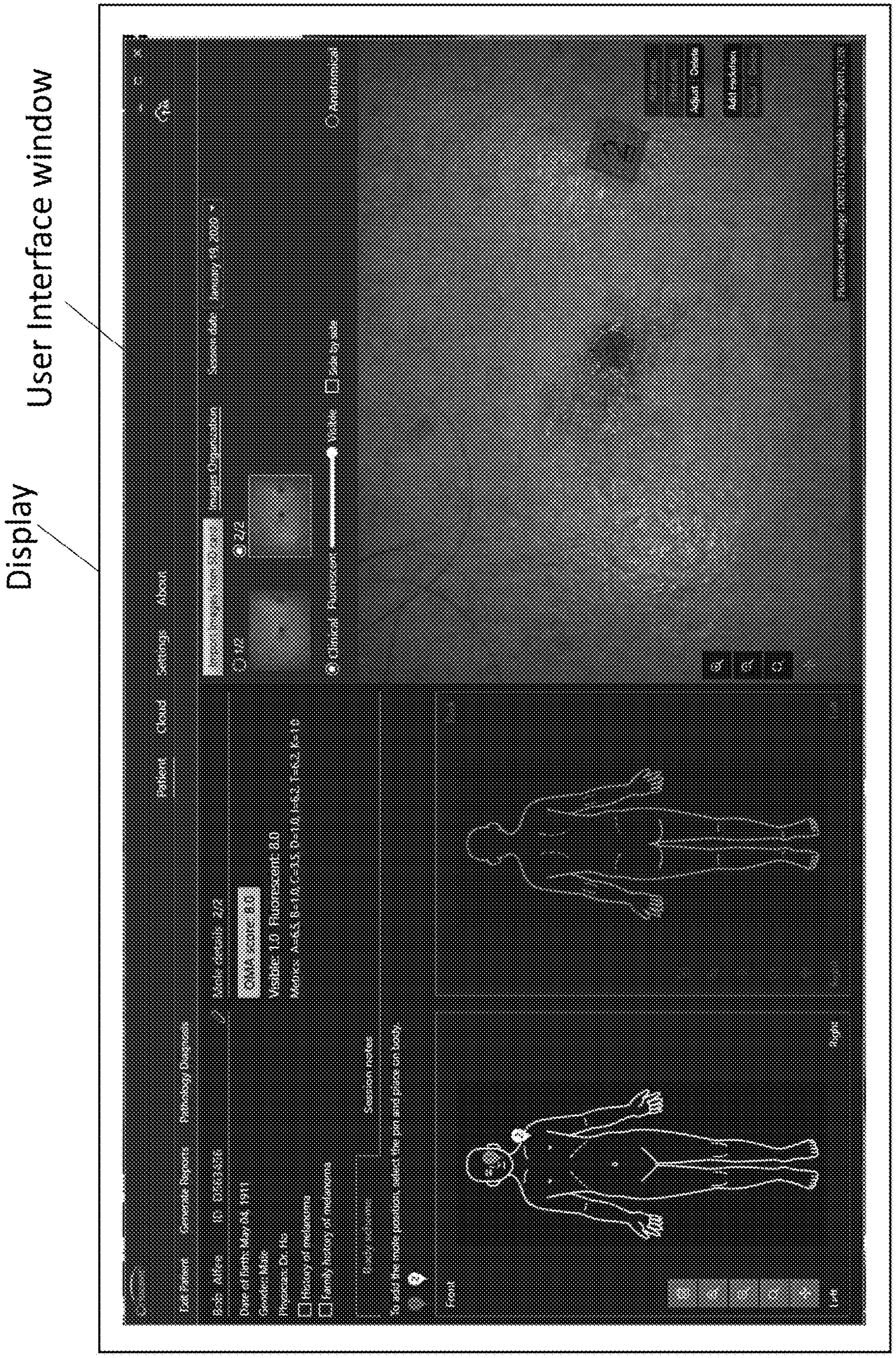
FIG. 10 shows an exemplary user interface depicting a patient card with visible light image displayed, in accordance with embodiments.
Figure 11:
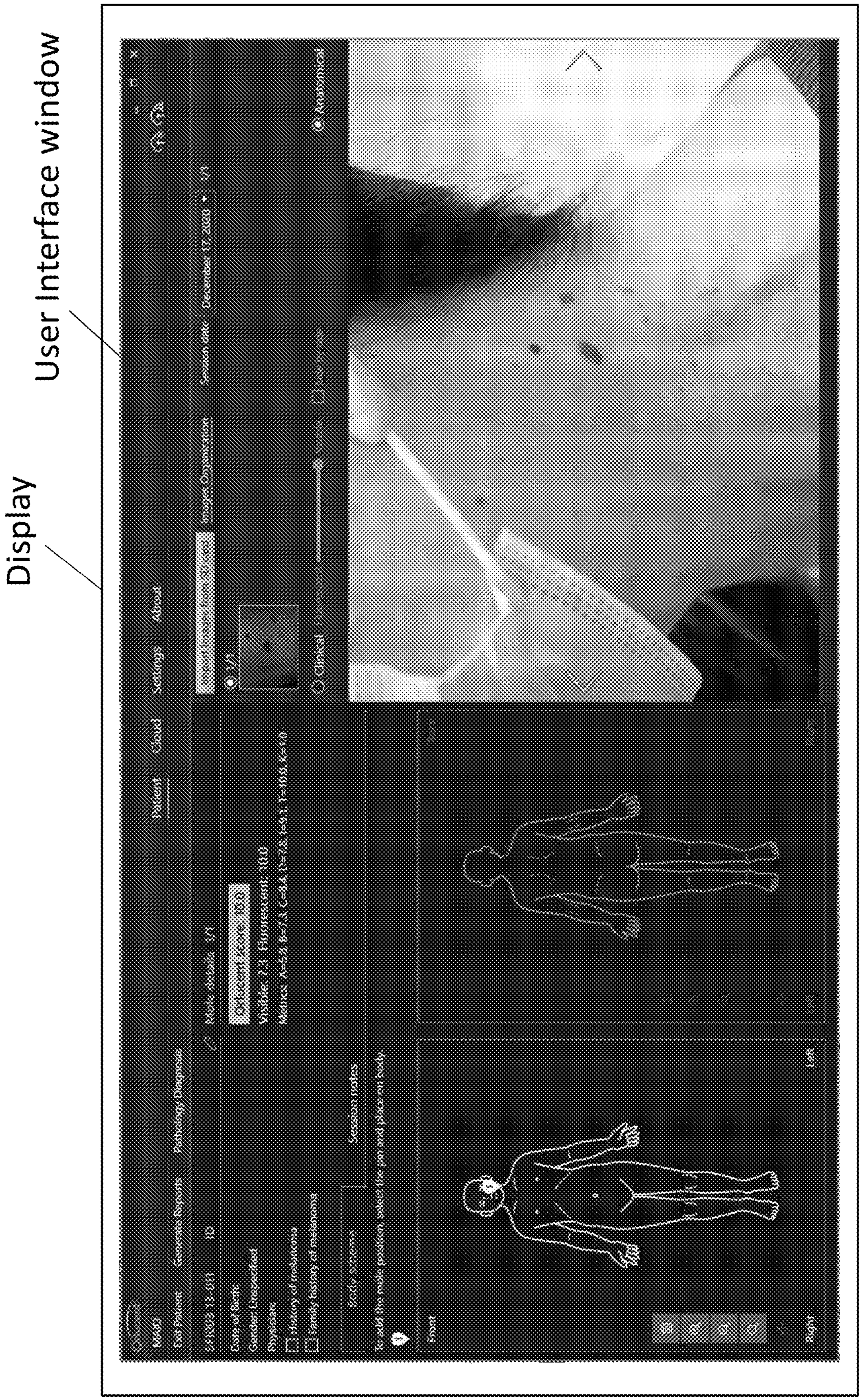
FIG. 11 shows an exemplary user interface depicting a patient card with anatomical image displayed, in accordance with embodiments.

At Step 308, the mole(s) may be mapped to the body locations of the patient using anatomical images (e.g., as shown in FIGS. 9-11). In some embodiments, the user may map the moles to the body locations by dragging the fiducials marker on a displayed body outline. In other embodiments, the moles may be mapped automatically. In some embodiments, mole mapping may be bypassed by the user and performed at a later time.

At Step 309, the images may be processed to identify mole boundaries. In some embodiments, the boundaries may be determined automatically. In some embodiments, the user may adjust the boundary using the user interface.

At Step 310, the images may be processed to calculate a mole analytics score as described further herein. In some embodiments, a visible score is calculated for the visible light image. In some embodiments, a fluorescent score is calculated for the fluorescent image. In some embodiments, an aggregate score is calculated from the visible light score and the fluorescent score. In some embodiments, the aggregate score may be the maximum of the visible light score and the fluorescent light score.

At Step 311, the mole analytics score may optionally be refined based on a machine learning algorithm. The machine learning algorithm may be, for example, an unsupervised learning algorithm, a supervised learning algorithm, or a combination thereof.

The unsupervised learning algorithm may include, for example, clustering, hierarchical clustering, k-means, mixture models, DBSCAN, OPTICS algorithm, anomaly detection, local outlier factor, neural networks, autoencoders, deep belief nets, hebbian learning, generative adversarial networks, self-organizing map, expectation-maximization algorithm (EM), method of moments, blind signal separation techniques, principal component analysis, independent component analysis, non-negative matrix factorization, singular value decomposition, or a combination thereof.

The supervised learning algorithm may include, for example, support vector machines, linear regression, logistic regression, linear discriminant analysis, decision trees, k-nearest neighbor algorithm, neural networks, similarity learning, or a combination thereof. In some embodiments, the machine learning algorithm may comprise a deep neural network (DNN).

The deep neural network may comprise a convolutional neural network (CNN). The CNN may be, for example, U-Net, ImageNet, LeNet-5, AlexNet, ZFNet, GoogleNet, VGGNet, ResNet18 or ResNet, etc. Other neural networks may include, for example, deep feed forward neural network, recurrent neural network, LSTM (Long Short Term Memory), GRU (Gated Recurrent Unit), Auto Encoder, variational autoencoder, adversarial autoencoder, denoising auto encoder, sparse auto encoder, boltzmann machine, RBM (Restricted BM), deep belief network, generative adversarial network (GAN), deep residual network, capsule network, or attention/transformer networks, etc.

In some embodiments, the machine learning algorithm may be, for example, a random forest, a boosted decision tree, a classification tree, a regression tree, a bagging tree, a neural network, or a rotation forest. The machine learning algorithm may be applied to a plurality of features extracted from the images.

In some embodiments, the neural network may comprise neural network layers. The neural network may have at least about 2 to 1000 or more neural network layers.

In some embodiments, the neural network may be trained using federated learning techniques.

Machine learning may be employed to measure the patient's image data similarity to training examples of melanoma data and benign data. The degree of similarity to these two sets of training exemplars may be reported in many different forms. For example, probability, feature set distance, weighted feature set distance, statistical measure of significance, and/or the like, to name a few. Regardless of the similarity measure reported by the machine learning algorithm, the system described herein may be configured to translate it to a common scoring format.

At Step 312, a mole analytics score report may be generated and displayed to the user (e.g., as shown in FIGS. 9-11). The mole analytics score report may include an assessment of the target region based on at least the optimal image pair. The assessment may comprise the mole analytics score(s). The assessment may be indicative of a probability of tissue remodeling at the target region. The probability of tissue remodeling may be associated with a probability of development of a tumor (e.g., melanoma if the target region includes a mole on a subject's skin). The assessment may be used to determine a clinical diagnosis or course of action based on the probability of development of a tumor in the target region (e.g., melanoma in the mole).

At Step 313, the user may import a pathology report and update the mole analytics report to incorporate the histological information.

Figure 17:
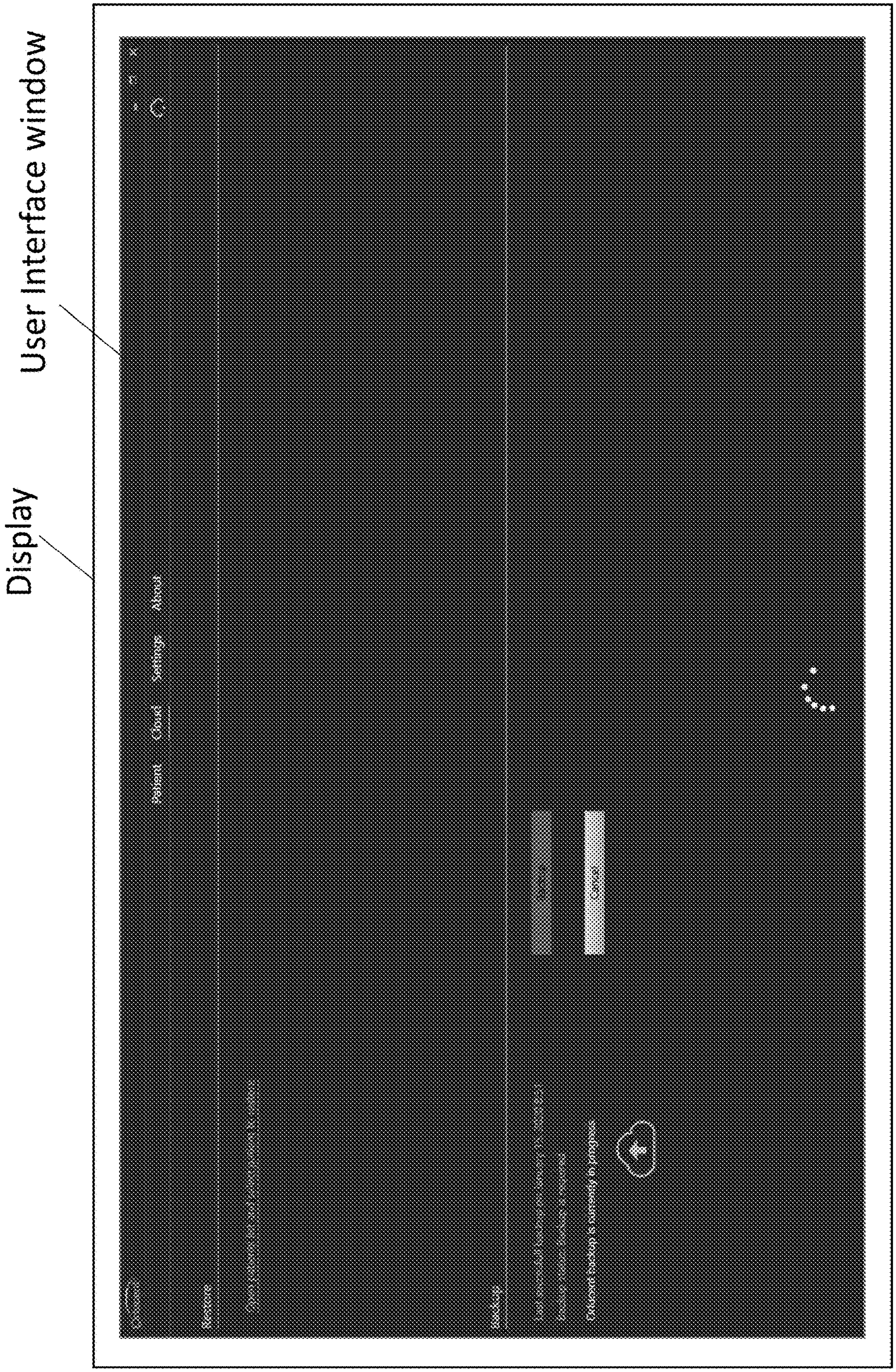
FIG. 17 shows an exemplary user interface depicting a backup in progress screen, in accordance with embodiments.

At Step 314, the data may optionally by automatically updated to a cloud-based storage unit (e.g., as shown in FIG. 17).

Figure 16:
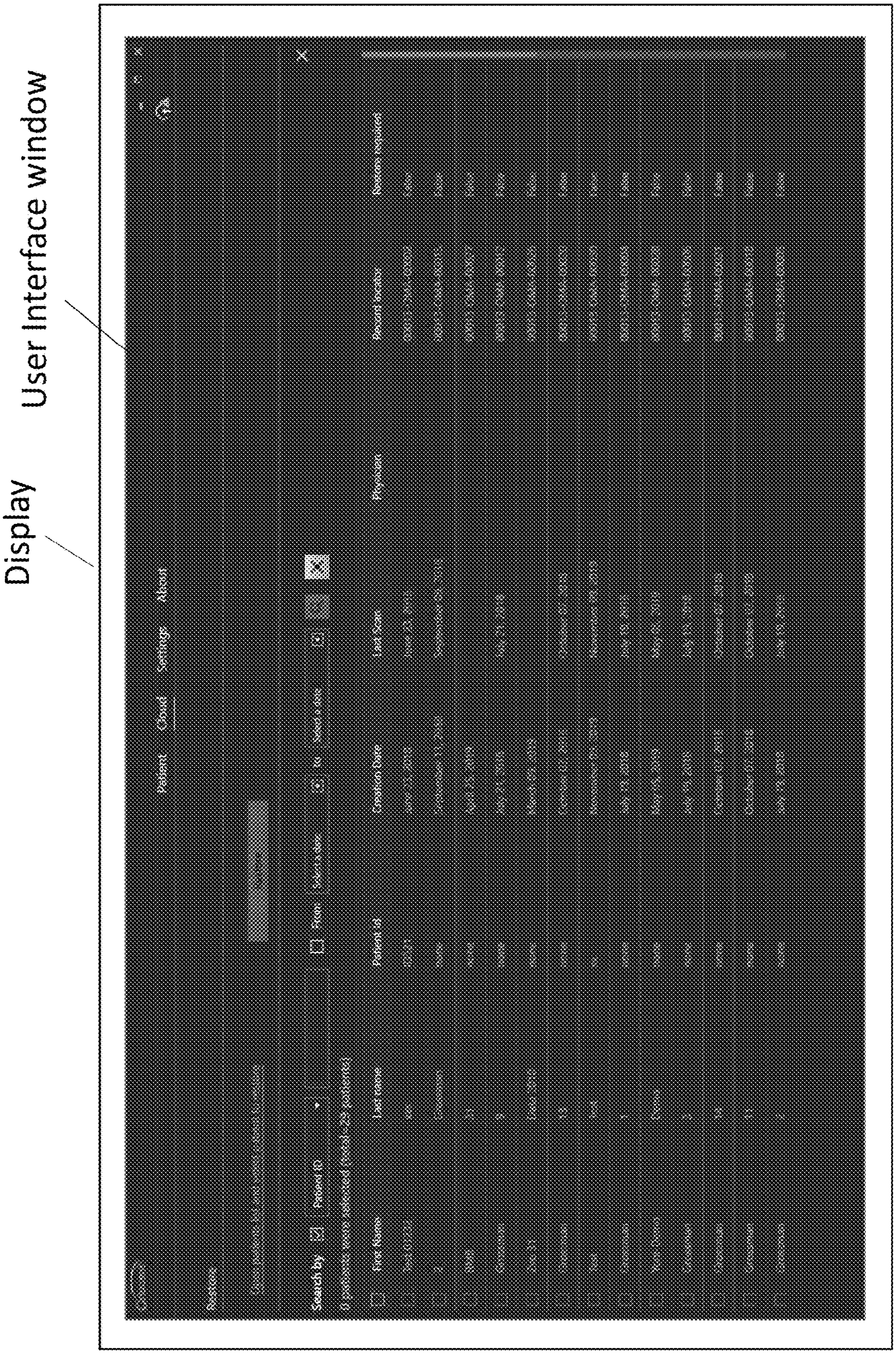
FIG. 16 shows an exemplary user interface depicting a restore from backup screen, in accordance with embodiments.

At Step 315, some or all of the data may optionally by automatically restored from a cloud-based storage unit (e.g., as shown in FIG. 16).

At Step 316, the data may be synchronized with a cloud-based storage unit (CLMS) using the unique patient identifier.

Although the steps above show a method 300 of operating a user interface to assess a risk of tissue remodeling for a pair of images in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to operate the user interface.

For example, in some embodiments Step 307 may occur in multiple steps such that a plurality of image pairs are identified and a user has the option of selecting or rejecting image pairs to identify the optimal image pair. The plurality of image pairs may be displayed to the user on the graphical user interface (e.g., sequentially displayed to the user) for selection or rejection in order of most to least optimal. Alternatively, or in combination, Step 307 optionally occurs automatically (e.g., without user input).

FIG. 4 shows an exemplary user interface depicting a login screen. The security of the login screen may be determined by a system administrator. For example, when the user is a clinician, the login screen may be HIPPA-compatible and may require a strong password to ensure security of patient data. Alternatively, when the user is a developer or other non-clinical user (using the portal for non-clinical data), the password requirements may be less secure in order to facilitate ease of use.

Figure 5:
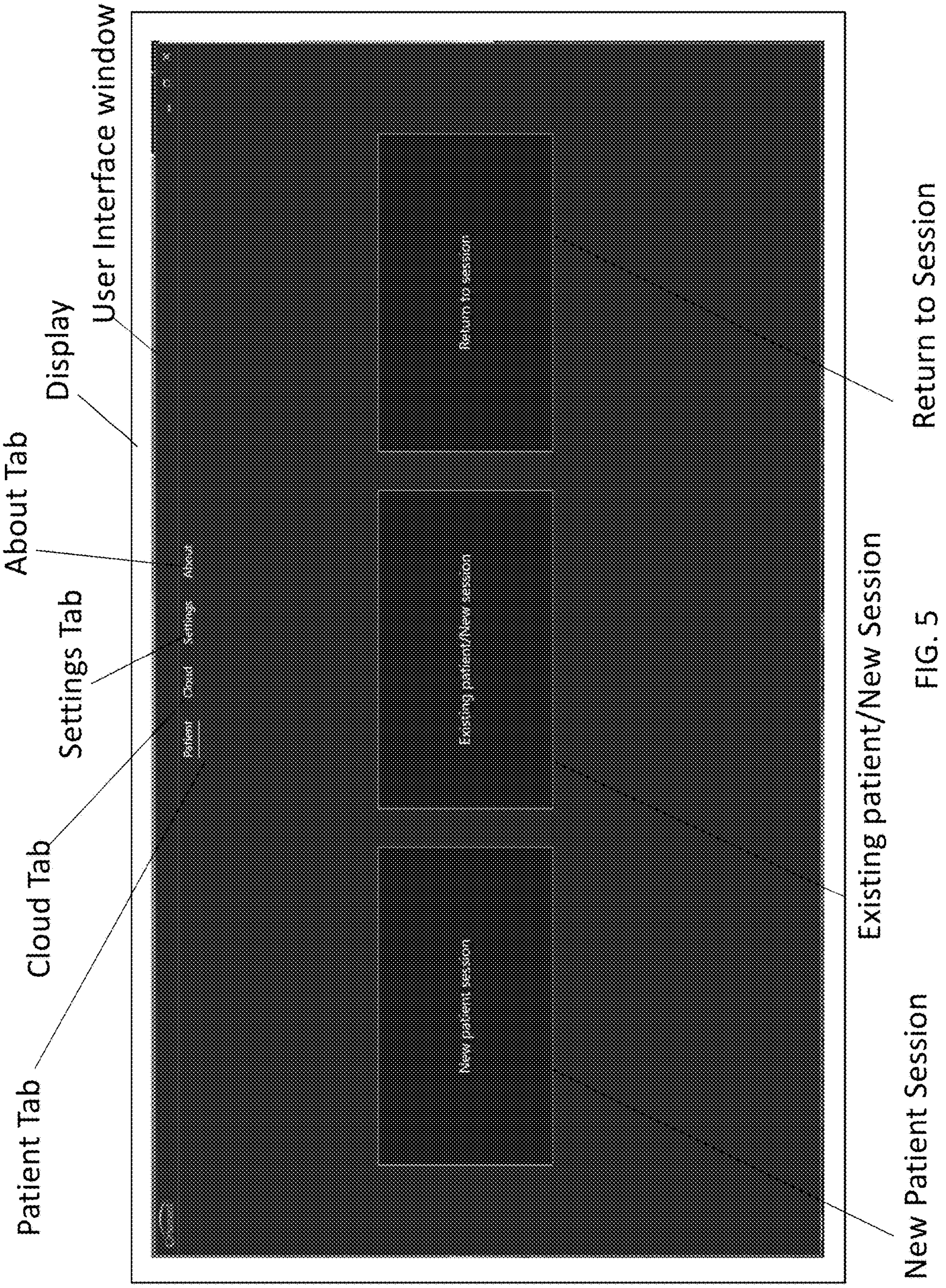
FIG. 5 shows an exemplary user interface depicting an initial menu, in accordance with embodiments.
Figure 12:
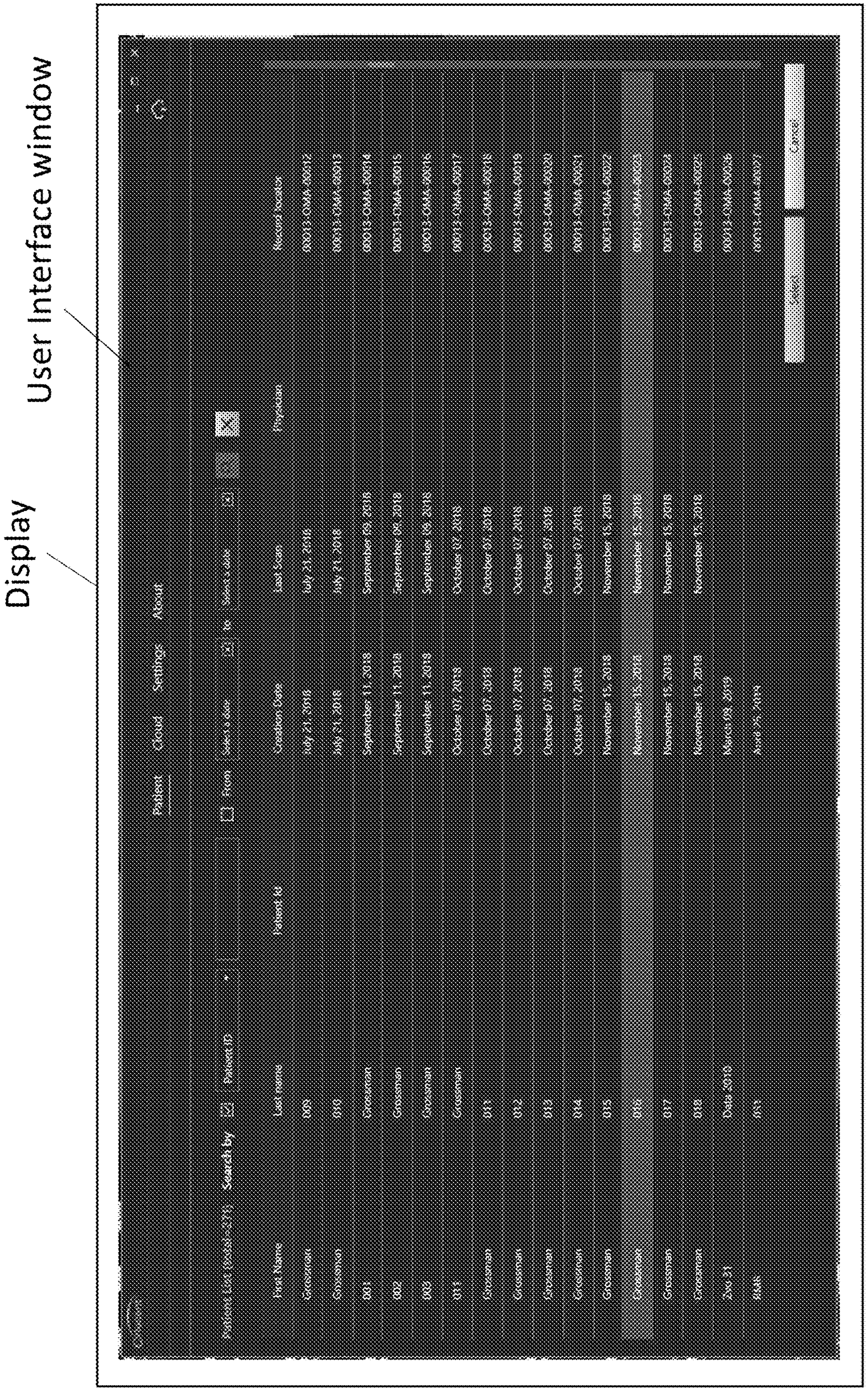
FIG. 12 shows an exemplary user interface depicting a patient history screen, in accordance with embodiments.

FIG. 5 shows an exemplary user interface depicting an initial menu. The initial menu may include a plurality of tabs for navigation. The tabs may include a patient tab, a cloud tab, a settings tab, and an about tab. The initial menu may be configured to display the patient tab as the default upon start-up. The patient tab may initially present a user with a screen having a plurality of buttons with choices for how to begin their session. The user may select to begin a new patient session, load an existing patient in a new session, or return to an in-progress session. Selecting the new patient session button may load a new session screen (e.g., as shown in FIG. 6). Selecting the existing patient/new session button may load a patient history screen (e.g., as shown in FIG. 12). Selecting the return to session button may open the current session's screen at the point where it was last saved/logged off.

FIG. 6 shows an exemplary user interface depicting a new patient input screen. The user may select the option to begin a new patient session on the initial menu screen shown in FIG. 5. A new patient input screen may then be displayed within the patient tab. The user may input information about the patient and their history (e.g., first name, last name, patient ID, date of birth, gender, physician, personal or family history of disease, etc.). The patient ID may be useful for synchronizing information with external software (e.g., clinic management software) and may be generated automatically or be input by the user to match the external software patient ID.

Figure 7:
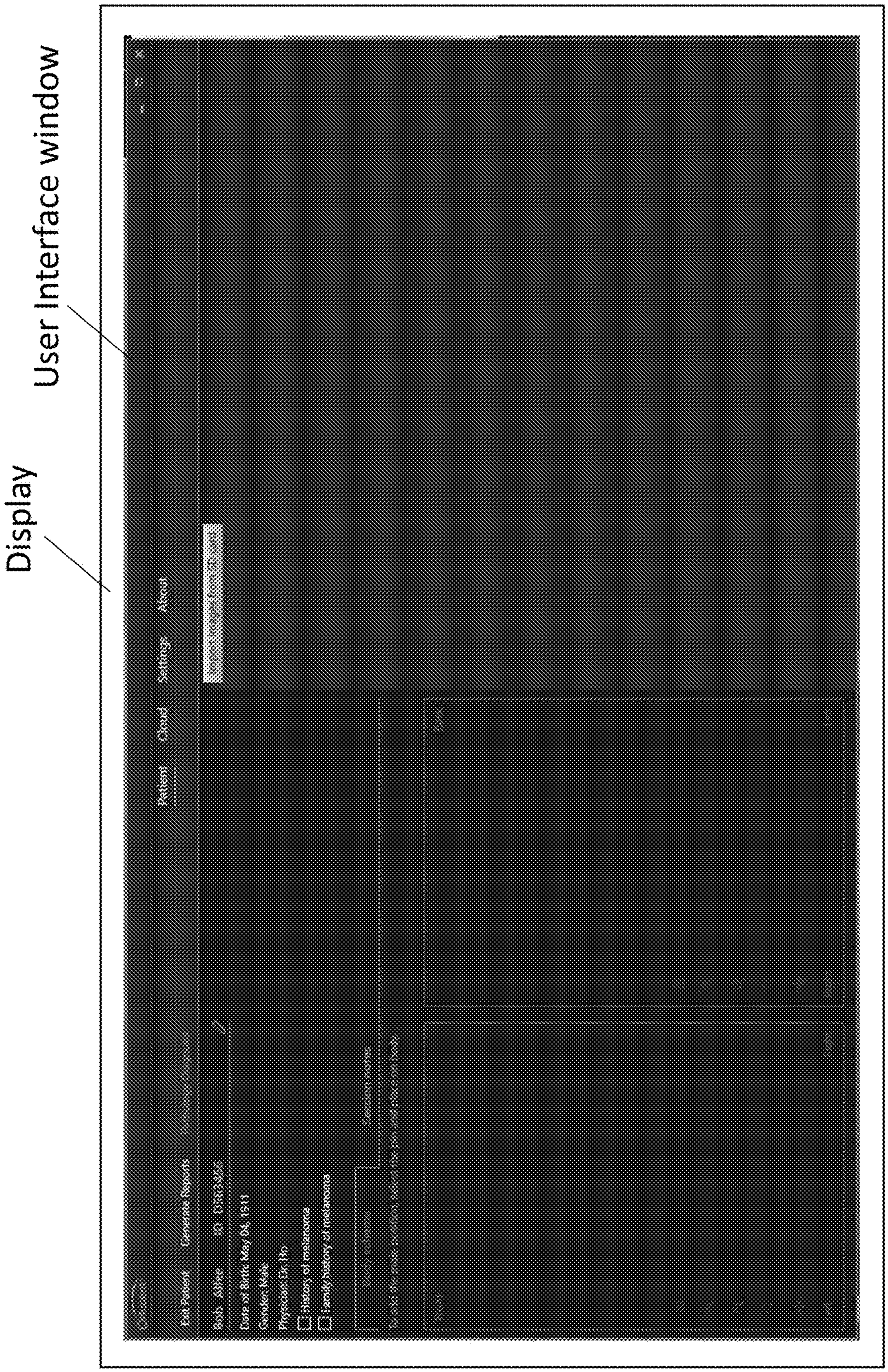
FIG. 7 shows an exemplary user interface depicting a new patient card before image import, in accordance with embodiments.

FIG. 7 shows an exemplary user interface depicting a new patient card before image import. Selecting "create" on the new patient input screen of FIG. 6 creates a new patient card. The new patient card includes patient information as well as areas for various images to be displayed and notes to be input by the user. Those areas may not be populated until the user imports images from a storage medium (e.g., an SD card).

FIG. 8 shows an exemplary user interface depicting an image import screen. Selecting "import images" on the new patient card screen of FIG. 7 allows the user to import patient images to the system. An optimal pair of visible and fluorescent images may be identified automatically for each mole and a unique fiducial number may be assigned to each mole. The optimal pair of images may be displayed to the user on the image import screen. The other imported images and/or anatomical images may also be displayed to the user on the image import screen. The user may be given the option to select or reject the first optimal image pair. If the user selects the first optimal image pair, the system may receive an input indicative of the user accepting the first optimal image pair and the first optimal image pair may be used for generating the assessment of the target region. If the user overrides the first optimal image pair, the system may receive an input indicative of the user rejecting the first optimal image pair and the imported images may be processed to determine a second optimal image pair which is different from the first optimal image pair. In some embodiments, the first and second optimal image pairs may not share any common images. Alternatively, the first and second optimal image pairs may share a common image (e.g., a common visible light image and/or a common fluorescent image). The second optimal image pair may be displayed and the user may be allowed to select or reject the image pair as previously described with respect to the first optimal image pair. Should the user select the second optimal image pair, the system may receive an input indicative of the user accepting the second optimal image pair and the second optimal image pair may be used for generating the assessment of the target region instead of the first optimal image pair. Should the user reject the second optimal image pair, the process may be repeated until an optimal image pair is selected. The optimal image pairs may be displayed sequentially until the user selects a desired pair.

In some embodiments, the image import screen may also display anatomical images assigned, e.g., by selecting an anatomical images tab to swap from the clinical images tab shown in FIG. 8. The screen may be substantially similar to the screen of FIG. 8, except that the assigned anatomical images may replace the unselected imported images after the optimal image pair has been selected by the user. For each set of clinical (fluorescent and visible light) image pairs there may be multiple anatomical images imported, which may aid the user in mapping the moles to one or more locations on the body. The anatomical images may automatically be assigned to the optimal image pair. The user may override the automatic selection as described herein. One or more anatomical images (preferably at least two) may be assigned to each optimal image pair. Once the anatomical images have been assigned for the first mole, the user may select the "next mole" button to import images for the next mole, etc. When all of the moles have been assigned an optimal image pair and anatomical images, the user may select the "import and calculate" button to process and display the images and/or tissue assessment to the user as described herein.

FIG. 9 shows an exemplary user interface depicting a patient card having an optimal image pair displayed side-by-side and tissue score(s). Once the optimal image pair and anatomical images for each mole have been selected or confirmed by the user, the images may be processed and displayed to the user. In some embodiments, the mole may be automatically detected within the target region and a graphical boundary or outline may be generated and displayed around the mole. The graphical boundary or outline may be automatically generated to follow a shape or contour of the mole. In some embodiments, the graphical boundary or outline may be adjustable or created by a user via the graphical user interface. The location of the mole(s) on the subject's body may be indicated on a schematic body diagram. The user may toggle between different moles, each having a unique fiducial identifier, and corresponding image sets as desired. The patient card may display the visible light image and the fluorescent image of the optimal image pair side-by-side for comparative viewing. A visible score, a fluorescent score, and an aggregate score may be automatically calculated after the image pair is selected for each mole and may be displayed to the user on the patient card. Metrics used to calculate the score for the visible light image may be displayed to the user on the patient card and may include, for example, the conventional "ABCD" mole criteria including asymmetry ("A"), border irregularity ("B"), color variegation ("C"), and diameter>6 mm ("D"). Metrics used to calculate the score for the fluorescent light image may be displayed to the user on the patient card and may include, for example, I/T measurements which include fluorescence intensity ("I") and texture ("T"). From our initial training data, it appears that, in at least some instances, exemplars of melanoma may exhibit clustering of ABCD metrics which differ from exemplars of benign. For example, exemplars of melanoma may exhibit clustering of I/T metrics which differ from exemplars of benign. A visible light score may be calculated as the Euclidean distance from the surface separating the melanoma and benign clusters of ABCD metrics. A fluorescent score may be calculated as the Euclidean distance from the surface separating the melanoma and benign clusters of I/T metrics. An aggregate score may be computed as the maximum of the visible score and the fluorescent score.

The visible light image and the fluorescent image may be adjusted and aligned to a set of coordinates within the optimal image pair. For example, the visible light image and the fluorescent image may be adjusted and aligned by rotating, translating, cropping, magnifying, and/or de-magnifying at least one or the visible light image and the fluorescent image. Alternatively, or in combination, the images may be aligned and adjusted using one or more fiducial markers present in both the visible light image and the fluorescent image. In some embodiments, the one or more fiducial markers may be annotated on the visible light image and the fluorescent image. Alternatively, or in combination, the one or more fiducial markers may be visible in both the visible light image and the fluorescent image. The fiducial markers may comprise one or more alphanumeric characters, a line, an edge, a dot, a two-dimensional shape, or the like, or any combination thereof. In some embodiments, the one or more fiducial markers may be provided at one or more predefined locations within the target region. In some embodiments, the one or more fiducial markers may be provided at a predefined distance and/or orientation relative to a location of the mole. The adjusted and aligned visible light image and fluorescent image may be displayed to the user on the patient card screen for ease of viewing.

The probability of tissue remodeling may be associated with a probability of development of a tumor (e.g., melanoma if the target region includes a mole on a subject's skin). For example, an aggregate score (here) of 7 or higher may indicate a probability of melanoma development. In some embodiments, one or more notifications (e.g., popup windows, highlighting, etc.) may be generated on the screen when the probability of tissue remodeling at the target region or the probability of tumor development (e.g., melanoma development) is greater than one or more predefined threshold values. It will be understood by one of ordinary skill in the art based on the teachings herein that the range of scores (e.g., 1-10) is non-limiting and may be defined as desired (e.g., arbitrarily or in accordance with medical grading nomenclature, etc.) in order to best capture and report the probability of interest for the target tissue of interest.

FIG. 10 shows an exemplary user interface depicting a patient card with visible light image displayed. The screen may be substantially similar to the screen in FIG. 9, except that the user interface may be configured to permit the user to toggle or switch between the visible light image or the fluorescent image within the optimal image pair to provide a two layer effect. The user may, for example, click on the word "fluorescent" to switch to the fluorescent image or "visible" to switch to the visible light image. Alternatively, or in combination, the user may use the slider to switch between images. In some embodiments, the slider may be operable to overlay the images to varying degrees (e.g., 50% visible and 50% fluorescent) at intermediate slider positions between "fluorescent" and "visible". Overlaying the images may enable the user to see where retention of the biotag occurs on the tissue surface relative to features that are visually apparent (e.g, a mole, lesion, etc.).

FIG. 11 shows an exemplary user interface depicting a patient card with anatomical image displayed. The screen may be substantially similar to the screen in FIG. 9, except that the anatomical image(s) may be displayed instead of the optimal image pair. The user may assign the anatomical image to a location on the schematic body diagram. For example, the user may place a fiducial marker on the schematic body diagram to assign the anatomical image of the target region including that fiducial marker to the desired location. The anatomical image may act as a reference image for the user and enable the user to distinguish between moles during the session as well as follow up on the same mole in another session.

FIG. 12 shows an exemplary user interface depicting a patient history screen. The patient history screen may be utilized to search through a patient list to find a particular patient, for example when loading data from an existing patient instead of creating a new patient card. The patient history screen may display information about the patient (e.g., first name, last name, patient ID, etc.) as well as other pertinent information about their history (e.g., date of file creation, date of last scan, physician name, record locator, etc.). The patient history screen may also enable a user to search for a patient, physician, session, etc., optionally within a specified date range.

Figure 13:
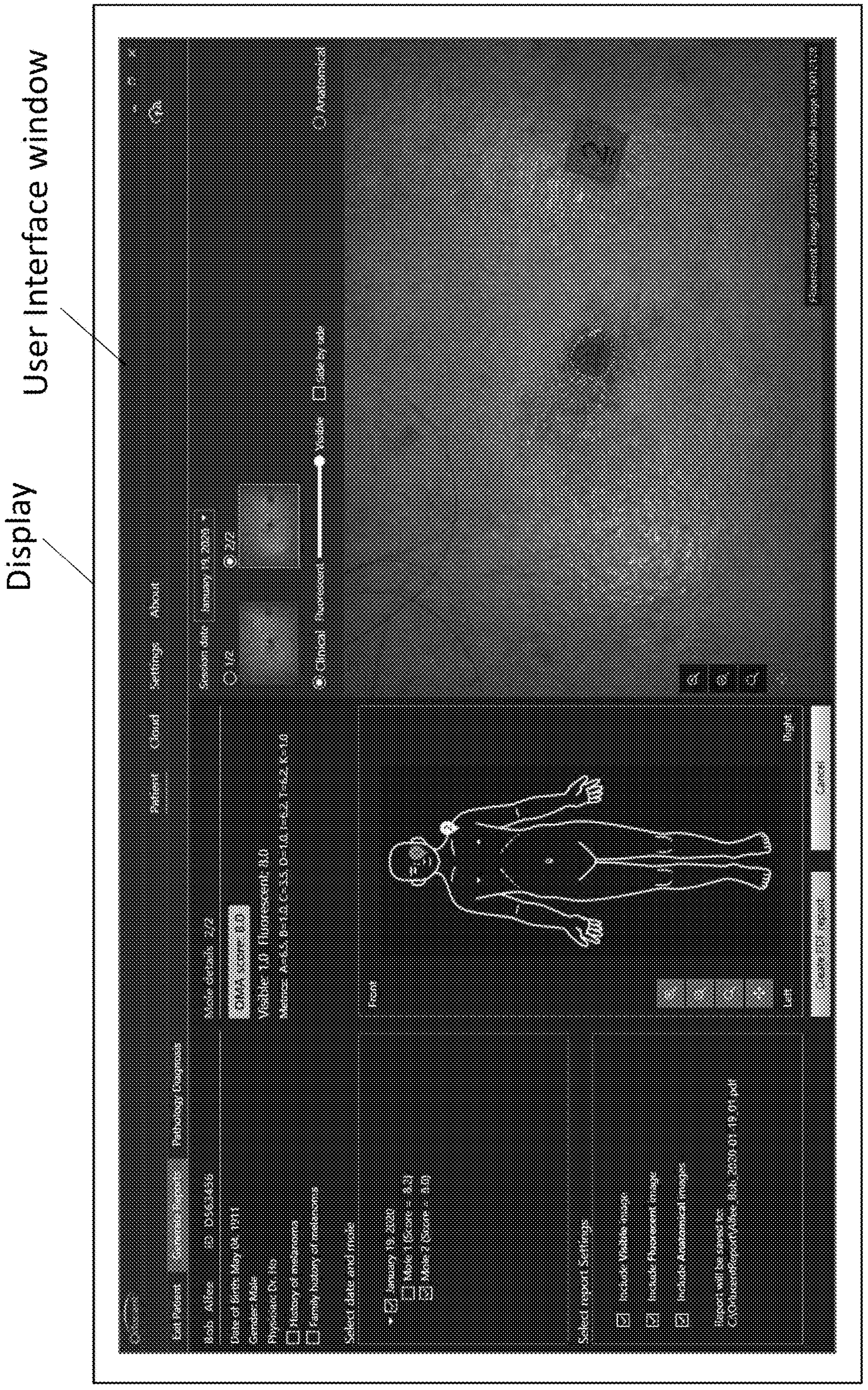
FIG. 13 shows an exemplary user interface depicting a generate report screen, in accordance with embodiments.

FIG. 13 shows an exemplary user interface depicting a generate report screen. The generate report screen may be configured to allow a user to generate a report (e.g., in pdf format) for printing and/or sharing with other users, e.g., for consultation. The generate report screen may be configured to allow the user to select the information to be included on the report. Such information may optionally include the mole(s) of interest, the visible light image, the fluorescent image, the anatomical image, the schematic body diagram, patient history, etc.

Figure 14:
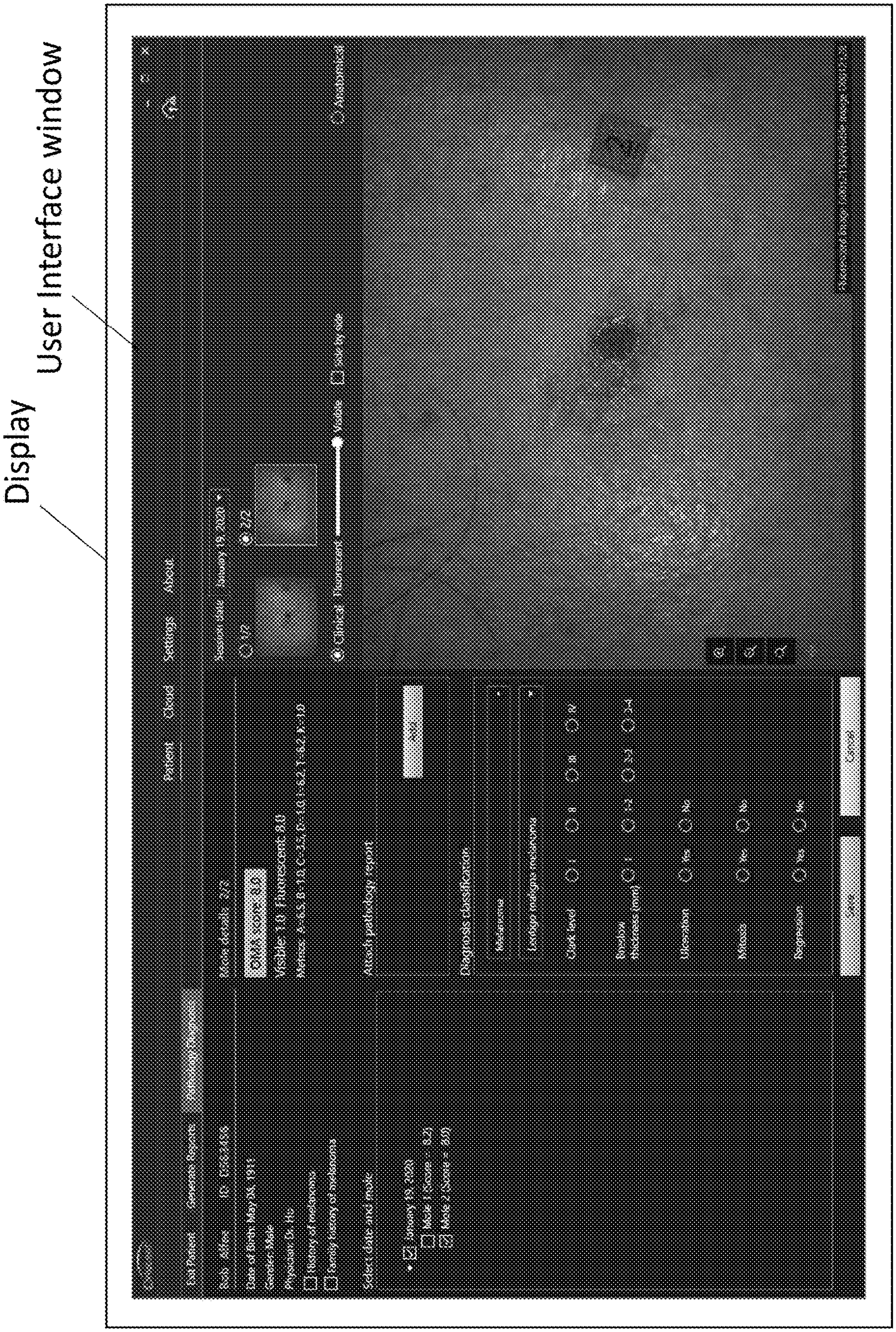
FIG. 14 shows an exemplary user interface depicting a pathology report input screen, in accordance with embodiments.

FIG. 14 shows an exemplary user interface depicting a pathology report input screen. The user may import a pathology report as a pdf file into the user interface. The user may then fill in the relevant information from the report. The relevant information for a mole may, for example, include the diagnosis classification, the Clark level, the Breslow thickness, the presence of ulceration, the presence of mitosis, and/or the presence of regression, or the like, or any combination thereon. In some embodiments, the relevant information may be automatically pulled from the pathology report into the program. In some cases, the diagnostic report from the pathologist may not be clear and the mole may be sent to multiple pathologists for examination. The user can then fill in the blanks using the dropdowns and/or radio groups based on their collation of the various reports. The pathology report results may be searchable. Correlation of the pathological diagnosis with the tissue remodeling score may enable further refinement of the scoring method (e.g., via machine-based learning).

Figure 15:
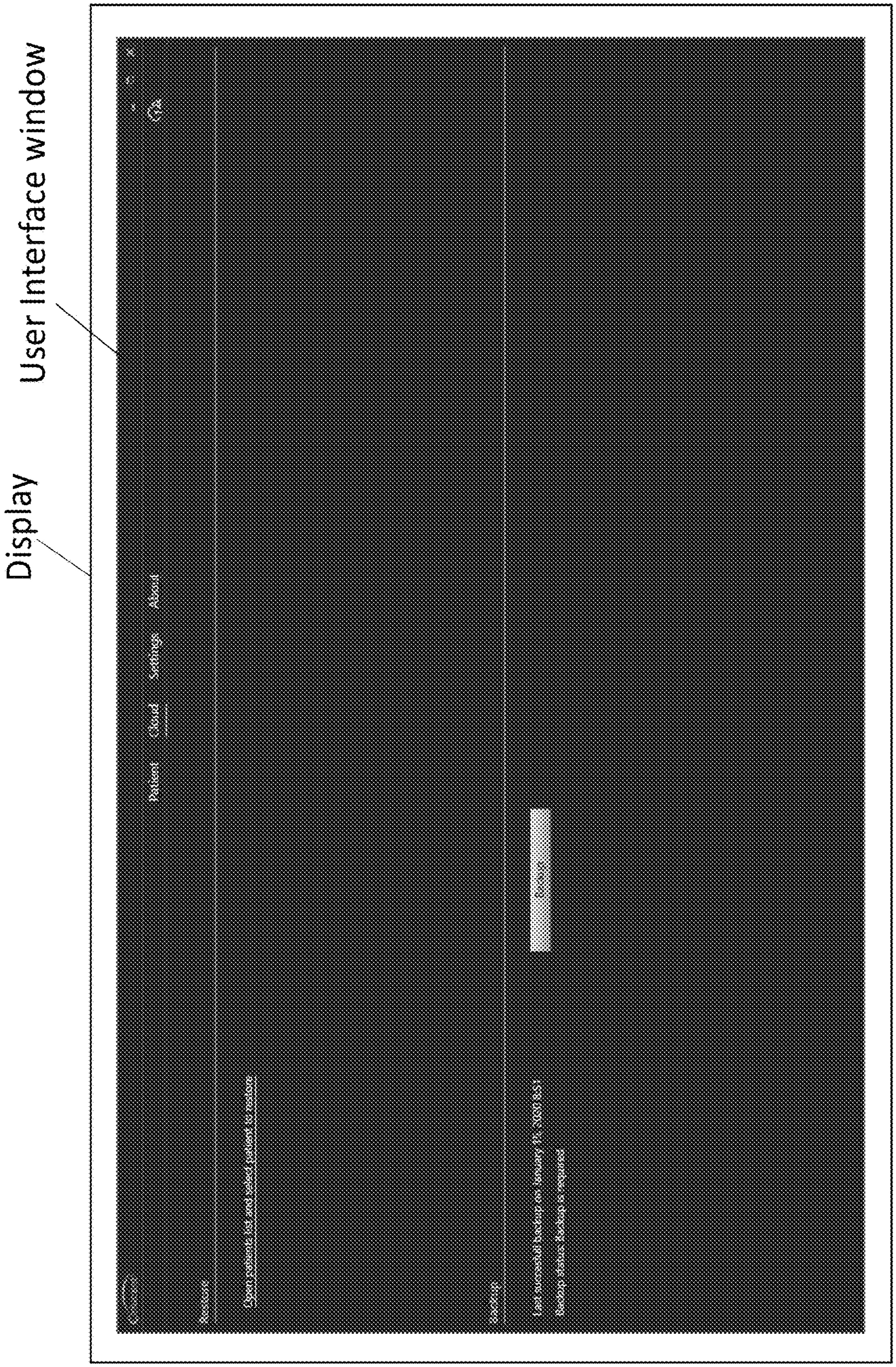
FIG. 15 shows an exemplary user interface depicting backup screen, in accordance with embodiments.

FIG. 15 shows an exemplary user interface depicting a backup screen. The backup screen may be accessed via a cloud tab. The user may backup and/or restore data safely from the cloud. The patient data may optionally be extracted and backed up on the cloud without any patient identifying information. Such data may then be used for machine-based learning as an example.

FIG. 16 shows an exemplary user interface depicting a restore from backup screen. The user may select the option to restore patient information from a backup on the backup screen shown in FIG. 15. A searchable patient list may then be displayed to the user and the user may select a patient and/or session to restore. The restore from backup screen may display information about the patient (e.g., first name, last name, patient ID, etc.) as well as other pertinent information about their history (e.g., date of file creation, date of last scan, physician name, record locator, etc.). The restore from backup screen may also enable a user to search for a patient, physician, session, etc., optionally within a specified date range. In some instances, a user may choose to restore data when a hardware or database issue has occurred on the local processor. The user may selectively restore patient data (e.g., restoring only a patient of interest, restoring only patients still with the clinic, restoring only patients arriving at the clinic that day, etc.) or restore the entire database.

FIG. 17 shows an exemplary user interface depicting a backup in progress screen. The user may select the option to backup their data to the cloud on the backup screen shown in FIG. 15. Alternatively, or in combination, cloud backup may be scheduled to occur automatically. All patient data stored locally may be backed up to the cloud.

It will be understood by one of ordinary skill in the art that the user interface described herein may have many variations in order to provide the user with a way to input data and read an output. For example, one or more of the tabs may be replaced with dropdown menus, toggles, or the like for navigation where desired to move between screens. Alternatively, or in combination, one or more of the dropdowns may be replaced with buttons, scroll bars, steppers, radio groups, switches, sliders, text boxes, or other input mechanisms. The user interface may comprise any number or any combination of organizational and/or input mechanisms as desired to provide the user with a simple, seamless experience and provide input variables to the system. The output may comprise one or more graphics, one or more assessments, one or more scores, or the like.

Figure 18:
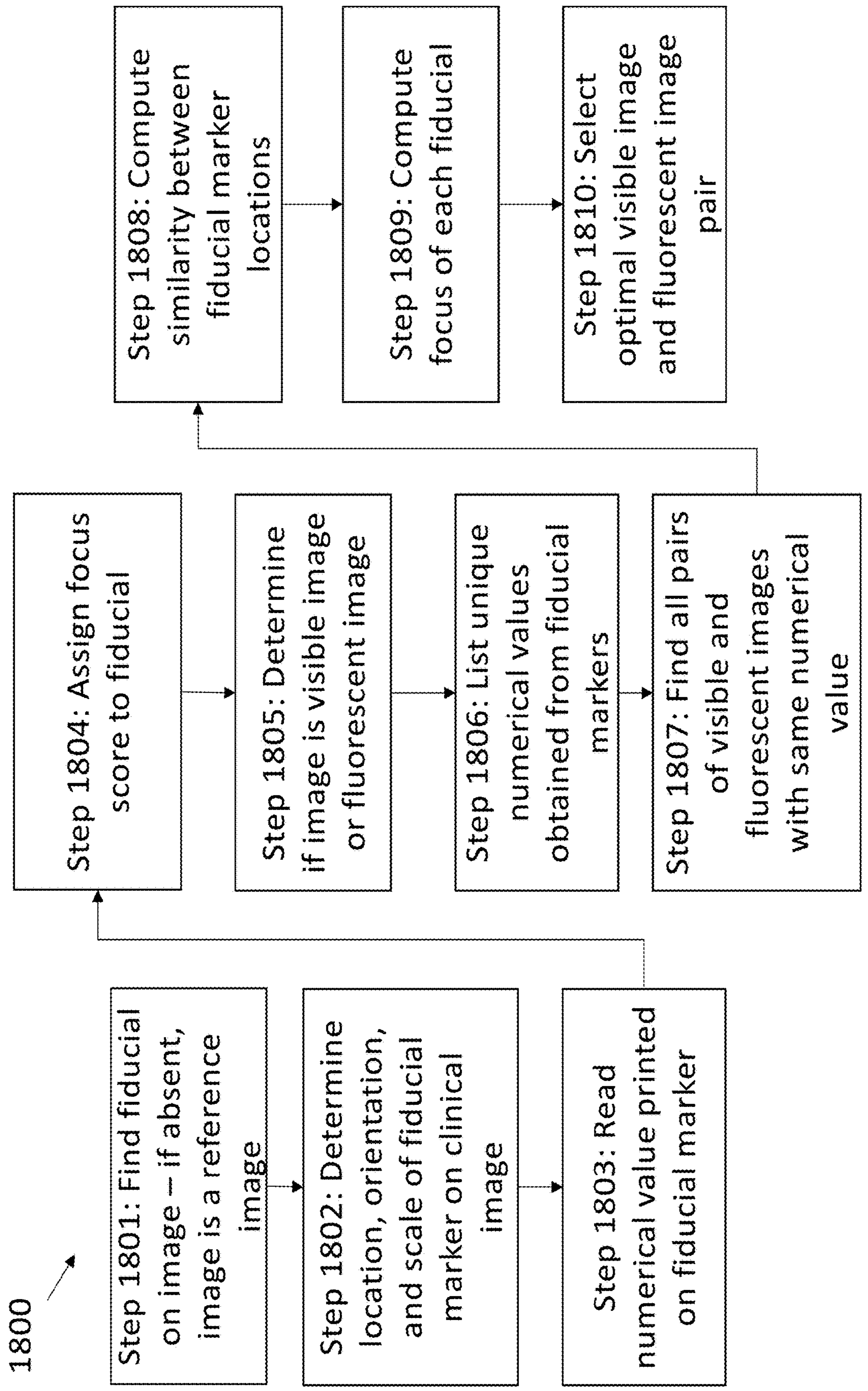
FIG. 18 shows a flowchart of a method for determining an optimal image pair, in accordance with embodiments.

FIG. 18 shows a flowchart of a method 1800 for determining an optimal image pair.

At Step 1801, for each image in a set of images, one or more fiducial markers may be identified. The image may be a visible image or a fluorescent image. If the fiducial marker is present, the image may be classified as a clinical image. If the fiducial marker is absent, the image may be classified as a reference image. In some embodiments, the target region may comprise a mole on the subject's skin and the plurality of images (visible and fluorescent) may be images of the mole. In some embodiments, the one or more fiducial markers identified on a fluorescent image may be the same as or different from the one or more fiducial markers identified on a visible light image.

At Step 1802, for each clinical image in a set of clinical images, the location, orientation, and scale of the fiducial marker may be determined.

At Step 1803, for each clinical image, the numerical value printed on the fiducial marker may be read.

At Step 1804, for each clinical image, a focus score may be assigned to the fiducial marker.

At Step 1805, for each clinical image, the image may be assessed to determine whether it is a fluorescent image or a visible image.

At Step 1806, a list may be generated using the unique numerical values obtained from the fiducial markers in Step 1803.

At Step 1807, all pairs of visible and fluorescent images with the same numerical value may be found within the set of clinical images.

At Step 1808, for each set of images with the same numerical value, the similarity between fiducial marker locations may be computed. The similarity may comprise the aggregate distance of the fiducial marker locations between the four corners of each image.

At Step 1809, for each image within the set of images with the same numerical value, the focus of each fiducial marker may be aggregated between the visible and fluorescent images.

At Step 1810, for each set of images with the same numerical value, the optimal visible image and fluorescent image pair may be selected. The optimal image pair may comprise a first visible light image selected from a set of visible light images. The optimal image pair may further comprise a first fluorescent image selected from a set of fluorescent images. The optimal image pair may have the most similarity in fiducial location as determined in Step 1808. If two pairs of images have the same similarity, the pair with the best focus as determined in Step 1809 may be selected as the optimal image pair.

Although the steps above show a method 1800 of identifying an optimal image pair in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to determine an optimal image pair.

For example, in some embodiments Step 1810 may occur in multiple steps such that a plurality of image pairs are identified and a user has the option of selecting or rejecting image pairs to identify the optimal image pair. Alternatively, or in combination, Step 1810 optionally occurs automatically (e.g., without user input).

Figure 19:
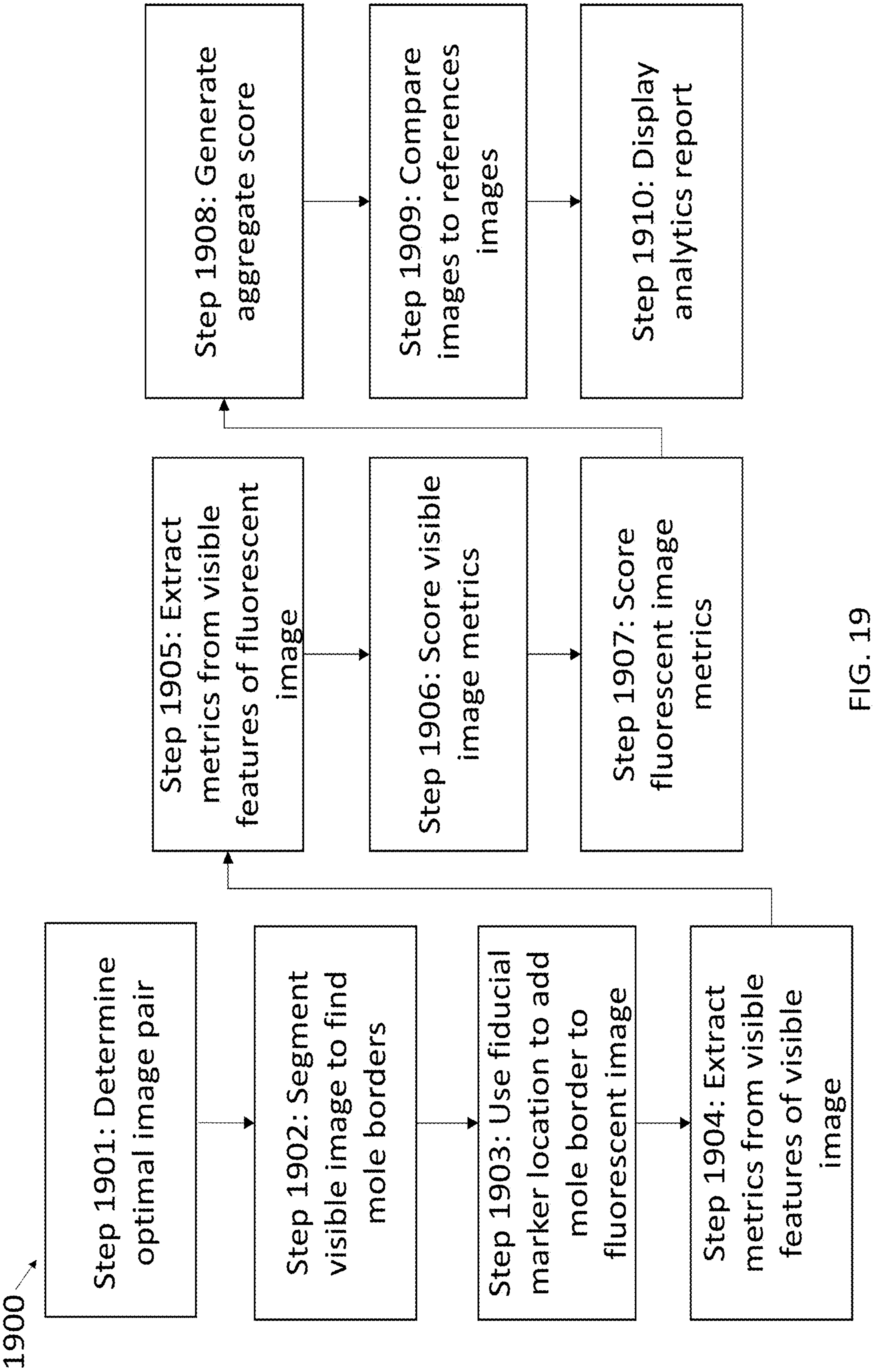
FIG. 19 shows a flowchart of a method for segmenting and scoring an optimal image pair, in accordance with embodiments.

In some embodiments, the plurality of images may be processed prior to, during, or after determining the optimal image pair. Processing the plurality of images may comprise at least one of the following: size filtering, normalization, standardization, reducing noise, elimination of imaging artifacts, background subtraction, cropping, magnification, resizing, repositioning, brightness adjustment, contrast adjustment, or object segmentation FIG. 19 shows a flowchart of a method 1900 for segmenting and scoring an optimal image pair.

At Step 1901, the plurality of images may be processed to determine an optimal image pair for the target region as described herein. The optimal image pair may comprise a first visible light image selected from a set of visible light images. The optimal image pair may further comprise a first fluorescent image selected from a set of fluorescent images. The visible light images and fluorescent light images may be obtained as described herein (e.g., as shown in FIG. 2). The optimal image pair may be selected to be complementary or matching with each other. The optimal image pair may be determined based on at least one or more of the following: focus quality, contrast, clarity, brightness, color, or resolution. Alternatively, or in combination, the optimal image pair may be determined from the plurality of images (visible and fluorescent) based at least on a position of the target region within each of the visible light images and each of the fluorescent images and/or based on a degree of similarity or correlation between each of the visible light images with each of the fluorescent images as described herein.

In some embodiments, processing the plurality of images may comprise at least one of the following: size filtering, normalization, standardization, reducing noise, elimination of imaging artifacts, background subtraction, cropping, magnification, resizing, repositioning, brightness adjustment, contrast adjustment, or object segmentation.

In some embodiments, a plurality of image pairs may be determined. The plurality of image pairs may comprise the optimal image pair. The optimal image pair may optionally be annotated to visually distinguish over the other image pairs. For example, the optimal image pair may be annotated by placing a predefined border around the optimal image pair displayed to the user (e.g., for selection or rejection by the user as described herein).

In some embodiments, the target region may comprise a mole on the subject's skin and the plurality of images (visible and fluorescent) may be images of the mole.

At Step 1902, the visible light image may be segmented to identify areas of interest. For example, when the target region comprises a mole, the visible light image may be segmented to find the borders of the mole. In some embodiments, the mole may be automatically detected within the target region and a graphical boundary or outline may be generated and displayed around the mole. The graphical boundary or outline may be automatically generated to follow a shape or contour of the mole. In some embodiments, the graphical boundary or outline may be adjustable or created by a user via the graphical user interface.

In some embodiments, the mole border may be identified automatically. Segmentation of the mole border from the visible image may begin by converting the visible image (e.g., an RGB image) into an intensity image. For each possible value of a threshold T, a mask of pixel values in the intensity image that are less than the threshold T may be created. The largest connected component in the mask may be found and any holes in the mask may be filled. Pixels on the mask boundary that are inside the mole may be identified. Pixels on the mask boundary that are outside the mole may be identified. The average contrast between the inside boundary pixels and the outside boundary pixels may be calculated. The threshold T which yields the largest average contrast may be identified. After the threshold T which yields the largest average contrast is identified, that threshold T may be used to segment the intensity image. Any holes in the segmented image may be filled. The mole outline may be refined by adjusting the mole border radially inwards or outward in order to maximize the local contrast. After adjusting each mole border pixel, the refine mole outline may be retained.

In some embodiments, the mole border may initially be identified by a user via the graphical user interface and then automatically refined. When a user (e.g., a clinician) creates a manual outline of the mole, the mole outline may be automatically refined by converting the visible image (e.g., an RGB image) into an intensity image. The outline created by the clinician may be used to segment the intensity image. Any holes in the segmented image may be filled. The mole outline may be refined by adjusting the mole border radially inwards or outward in order to maximize the local contrast. After adjusting each mole border pixel, the refine mole outline may be retained.

At Step 1903, the fiducial marker location (e.g., identified during determination of the optimal image pair) may be used to transform the mole border identified in Step 1902 from the visible light image to the fluorescent light image of the optimal image pair. In some embodiments, one or more fiducial markers may be identified on the fluorescent image of the optimal image pair and one or more fiducial markers may be identified on the visible light image of the optimal image pair. The one or more fiducial markers may be the same as or different from the one or more fiducial markers identified on the visible light image.

At Step 1904, a first set of metrics may be extracted from the visible features of the visible light image. The first set of metrics may comprise one or more of the following: size, shape, volume, color, or surface texture of the mole and its surrounding area. The visible light image may be segmented as described herein and the first set of metrics may comprise metrics from one or more segments as described herein. For example, a macro region surrounding the mole may be segmented as described herein.

At Step 1905, a second set of metrics may be extracted from the visible (e.g., fluorescent) features of the fluorescent image. The second set of metrics may comprise one or more of the following: size, shape, area or extent of tissue remodeling, pixel intensity, fluorescence intensity, or patterns or textures in the target region beneath the subject's skin and surrounding the mole. The fluorescent light image may be segmented as described herein and the first set of metrics may comprise metrics from one or more segments as described herein. For example, a macro region surrounding the mole may be segmented as described herein.

At Step 1906, the visible image metrics may be scored to generate a visible score.

At Step 1907, the fluorescent image metrics may be scored to generate a fluorescent score.

At Step 1908, an aggregate score may be generated for the optimal image pair. The aggregate score may be indicative of tissue remodeling activity. The aggregate score may be a composite of two or more discrete scores. For example, the aggregate score may be a composite of the visible score for the visible light image and the fluorescent score for the fluorescent light image. In some embodiments, the two or more discrete scores may be weighted equally such that the score for the visible light image and the score for the fluorescent image are both given the same weight. Alternatively, the two or more discrete scores may be weighted differently such that the score for the visible light image and a score for the fluorescent image are given different weights. In some embodiments, the score for the fluorescent image may be given a higher weight than the score for the visible light image. Alternatively, the score for the fluorescent image may be given a lower weight than the score for the visible light image.

The aggregate score may be a numerical score along a scale that may provide the likelihood of tissue remodeling. In some embodiments, the aggregate score may lie within a value range. In some embodiments, the two or more discrete scores may lie within a value range. In some embodiments, the score for the visible light image and the score for the fluorescent image are based on a standardized value range.

The probability of tissue remodeling may be associated with a probability of development of a tumor (e.g., melanoma if the target region includes a mole on a subject's skin).

The aggregate score may, for example, lie within a range from 0 to 10. A low score may indicate a low probability of tissue remodeling. A high score may indicate a high probability of tissue remodeling. For example, a score of 5 and above may indicate probably tissue remodeling. In some instances, a score of 7 or above may further indicate a probability of melanoma. In some embodiments, the aggregate score may be a combination of visible score calculated from the ABCD metrics calculated from the visible image and the fluorescent score calculated from the I/T metrics calculated from the fluorescent image.

At Step 1909, the optimal image pair may be compared to one or more reference images, for example a reference image pair. The reference image pair may comprise a visible light reference image that is not from the set of visible light images (e.g., a visible light reference image from an earlier session with the same patient or from a different patient entirely). The reference image pair may further comprise a fluorescent reference image that is not from the set of fluorescent images. In some embodiments, the reference image pair may or may not comprise fiducial markers. For example, the optimal image pair may comprise one or more fiducial markers and the reference image pair may not comprise fiducial markers. Alternatively, the optimal image pair may comprise a first set of fiducial markers located a predefined location and/or orientation relative to the target region (e.g., relative to a mole) and the reference image pair may comprise a set of fiducial markers located near a boundary of each reference image within the reference image pair. In some embodiments, the reference image pair may comprise a photograph of the target region anatomy (e.g., a shoulder with a mole on it) and/or a schematic body diagram. The reference image pair may be used by the user to find the location of the mole on the body.

At Step 1910, an analytics report may be generated and displayed as described herein. The analytics report may include an assessment of tissue remodeling and/or the probability of tumor development as described herein. In some embodiments, the analytics report may be useable (alone or in combination with standard techniques) to determine a clinical diagnosis and/or course of action based on the probability of development of melanoma in the mole.

Although the steps above show a method 1900 of identifying, segmenting, and scoring an optimal image pair in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to score an optimal image pair.

For example, in some embodiments Step 1901 may occur in multiple steps such that a plurality of image pairs are identified and a user has the option of selecting or rejecting image pairs to identify the optimal image pair. Alternatively, or in combination, Step 1901 optionally occurs automatically (e.g., without user input).

Figure 20:
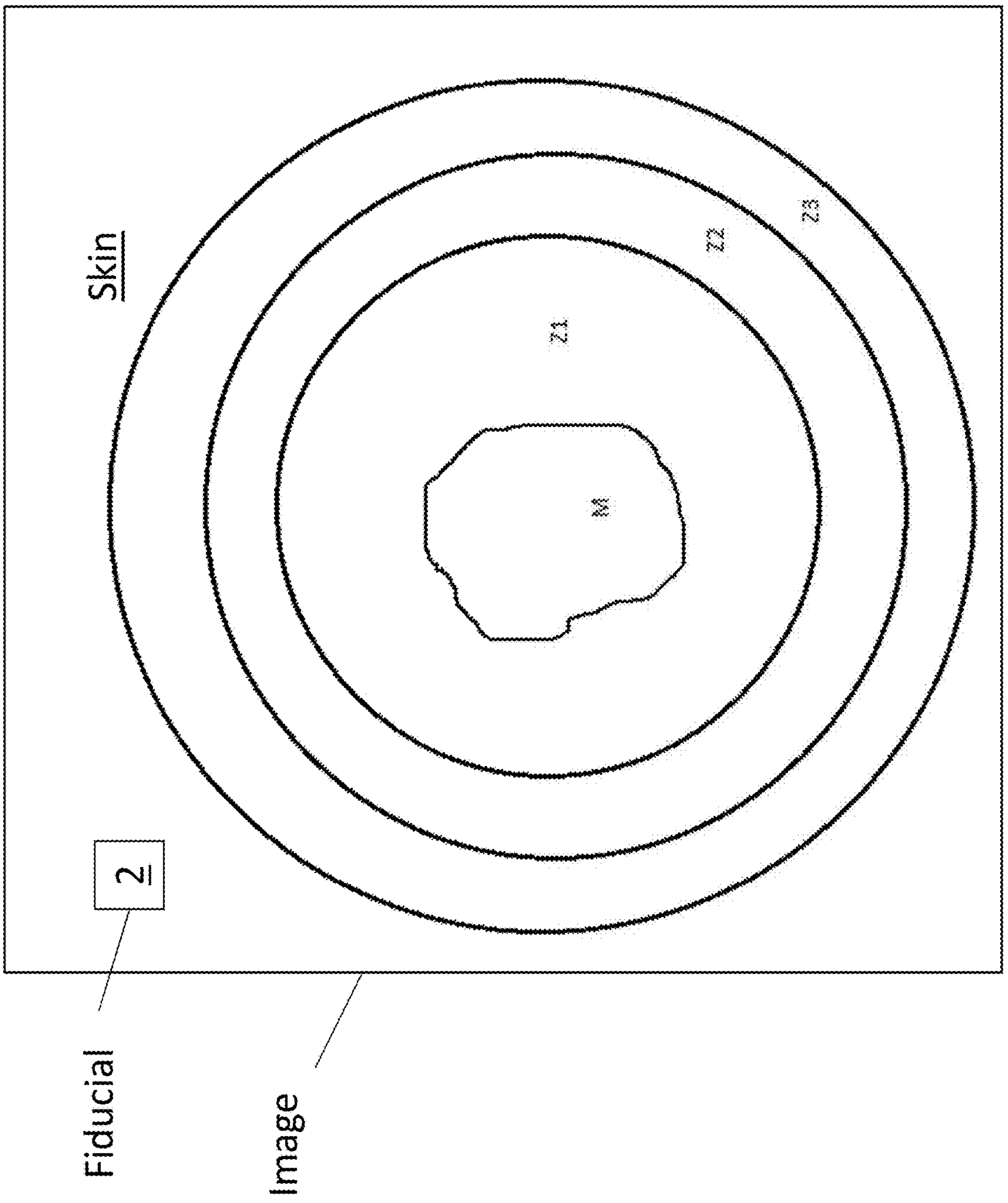
FIG. 20 shows an image of a mole and surrounding skin divided into a plurality of segments, in accordance with embodiments.
Figure 21:
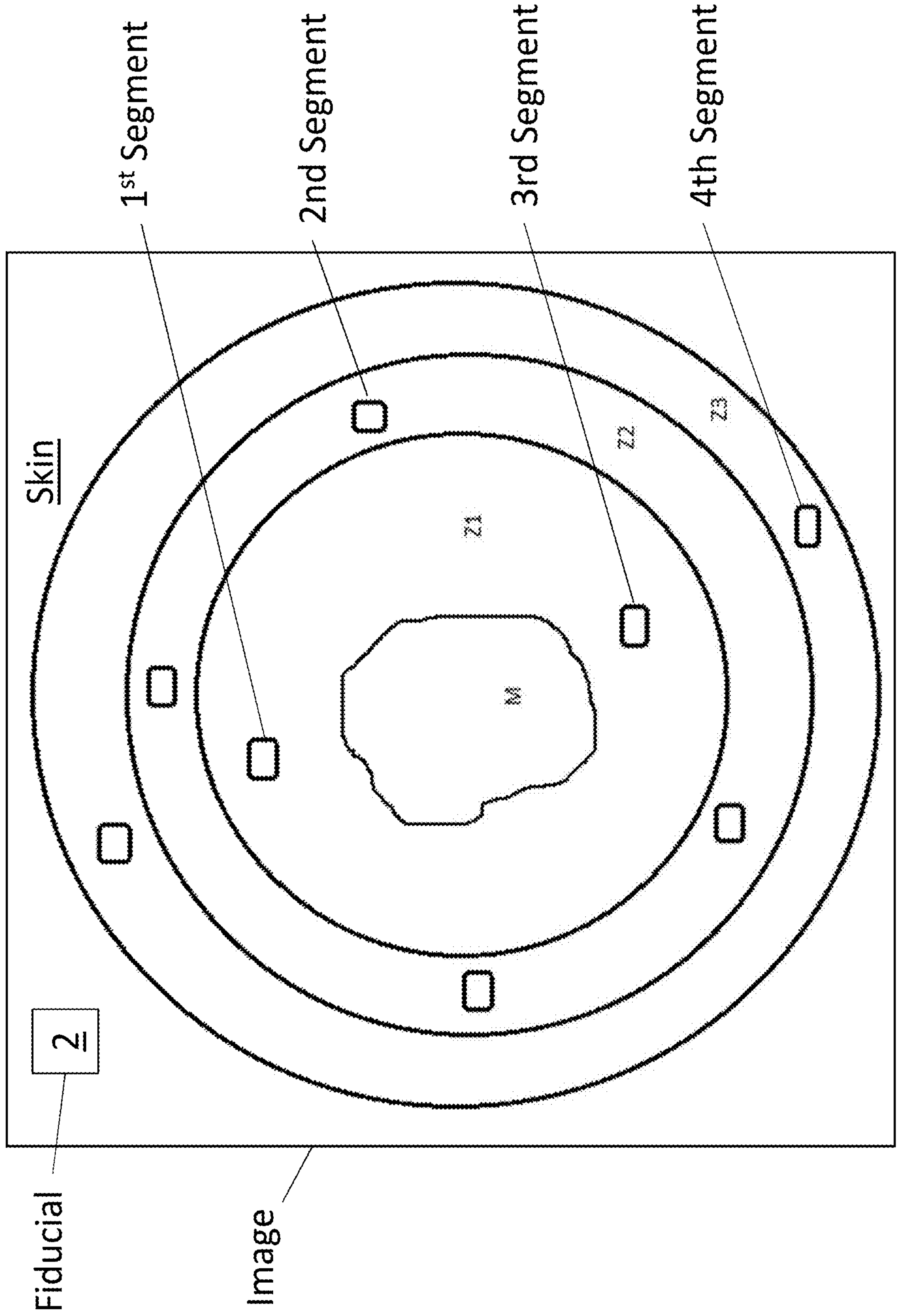
FIG. 21 shows an image of a mole and surrounding skin divided into a plurality of segments and sub-regions, in accordance with embodiments.

FIG. 20 shows an image of a mole and surrounding skin divided into a plurality of segments. FIG. 21 shows an image of a mole and surrounding skin divided into a plurality of segments and sub-regions. A fiducial marker may be placed on the skin adjacent the mole as described herein. Segmentation of the macro region around the mole into smaller localized regions may improve scoring accuracy and/or reduce false positives compared to analyzing the macro region as a whole. The skin surrounding the mole M, also referred to herein as the macro region, may be segmented into a plurality of segments for analysis. For example, a first segment or zone Z1 of the image may comprise the region of the skin immediately surrounding the mole M. A second segment or zone Z2 may be radially outward from the first zone Z1 and may comprise tissue of the macro region second closest to the mole. A third segment or zone Z3 may be radially outward from the second zone Z2, a fourth segment may be radially outward from the third segment, and so on. In some embodiments, the macro region may be segmented in both the visible light image and the fluorescent image of the optimal image pair. In some embodiments, the macro region may be segmented for analysis only in the fluorescent image. The segmented images may be analyzed to identify the intensity of the biotag retention in the surrounding macro region and/or the pattern of its retention in the target region (mole and/or macro region), or for any other feature desired by one of ordinary skill the art.

For example, a fluorescent image may be segmented and analyzed to identify the intensity and texture of the biotag retention in the target region and the macro region. The red channel (or any other channel corresponding to the fluorescent signature of the biotag) may be extracted from the fluorescent image. The location of the fiducial marker 2 may be used to transform the mole border from the corresponding visible image to the red channel of the fluorescent image as described herein. The mole border may be used to create a mask to indicate the location of the mole in the fluorescent image. Concentric regions surrounding the mole may be generated to segment the mole into segments or zones (e.g., zones Z1, Z2, Z3, etc.) as shown in FIG. 20. The segments or zones Z1, Z2, Z3, etc. may contain the signal generated by the biotag. In some embodiments, the concentric regions may be concentric rings spaced the same or different distance apart. Alternatively, in some embodiments, the concentric regions may mimic the border of the mole and may be generated using a distance map to define the distance from the mole border. Each segment or zone may be divided into sub-regions as shown in FIG. 21. The sub-regions may vary by number, size, location, and amount of overlap with adjacent sub-regions. In some embodiments, the segments or zones may be divided into sub-regions based on an angle from the center of the mole. Each segment of zone may comprise one or more sub-regions, for example a plurality of sub-regions. The intensity of each sub-region may be measured. The sub-region with the largest intensity may yield the intensity metric value. In many embodiments, the segment or zone Z2 second closest to the mole M may reliably contain uniform biotag retention and the smallest intensity sub-region in zone Z2 may be identified. In some embodiments, Zone Z1 may be too close to the mole boundary and pigment inside the mole may obscure the fluorescent signal. Zone Z3, on the other hand, may be too far from the mole and might not have received any biotag. Zone Z2 may be far enough away from the mole so it is not affected by mole pigment or lack of biotag. The texture metric may be calculated from the largest intensity sub-region of the image and the smallest intensity sub-region of zone Z2. The texture metric may be the difference in intensity between subregions that have received biotag.

Computer Control Systems

Figure 22:
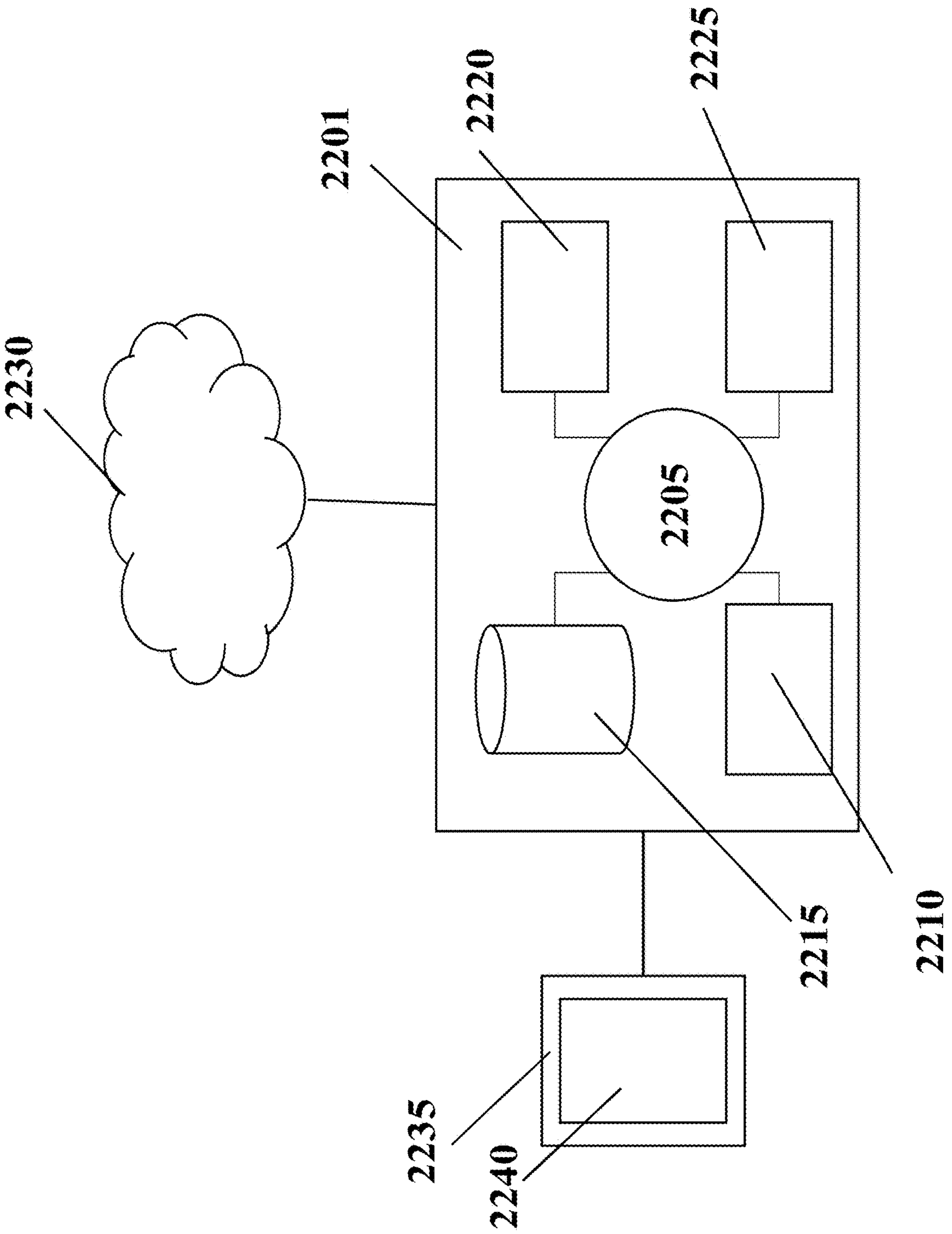
FIG. 22 shows a computer control system that is programmed or otherwise configured to implement methods provided herein, in accordance with embodiments.

The present disclosure provides computer control systems that are programmed to implement methods of the disclosure. FIG. 22 shows a computer system 2201 that is programmed or otherwise configured to assess tissue remodeling risk. The computer system 2201 can regulate various aspects of any of the methods to determine the risk of tissue remodeling of the present disclosure, such as, for example, processing a plurality of images to determine an optimal image pair, analyzing the images for tissue remodeling, scoring the images, transforming the images and scores into a tangible visible output such as a risk and/or extent of tissue remodeling. The computer system 2201 can be an electronic device of a user or a computer system that is remotely located with respect to the electronic device. The electronic device can be a mobile electronic device.

The computer system 2201 includes a central processing unit (CPU, also "processor" and "computer processor" herein) 2205, which can be a single core or multi core processor, or a plurality of processors for parallel processing. The computer system 2201 also includes memory or memory location 2210 (e.g., random-access memory, read-only memory, flash memory), electronic storage unit 2215 (e.g., hard disk), communication interface 2220 (e.g., network adapter) for communicating with one or more other systems, and peripheral devices 2225, such as cache, other memory, data storage and/or electronic display adapters. The memory 2210, storage unit 2215, interface 2220 and peripheral devices 2225 are in communication with the CPU 2205 through a communication bus (solid lines), such as a motherboard. The storage unit 2215 can be a data storage unit (or data repository) for storing data. The computer system 2201 can be operatively coupled to a computer network ("network") 2230 with the aid of the communication interface 2220. The network 2230 can be the Internet, an internet and/or extranet, or an intranet and/or extranet that is in communication with the Internet. The network 2230 in some cases is a telecommunication and/or data network. The network 2230 can include one or more computer servers, which can enable distributed computing, such as cloud computing. The network 2230, in some cases with the aid of the computer system 2201, can implement a peer-to-peer network, which may enable devices coupled to the computer system 2201 to behave as a client or a server.

The CPU 2205 can execute a sequence of machine-readable instructions, which can be embodied in a program or software. The instructions may be stored in a memory location, such as the memory 2210. The instructions can be directed to the CPU 2205, which can subsequently program or otherwise configure the CPU 2205 to implement methods of the present disclosure. Examples of operations performed by the CPU 2205 can include fetch, decode, execute, and writeback.

The CPU 2205 can be part of a circuit, such as an integrated circuit. One or more other components of the system 2201 can be included in the circuit. In some cases, the circuit is an application specific integrated circuit (ASIC).

The storage unit 2215 can store files, such as drivers, libraries and saved programs. The storage unit 2215 can store user data, e.g., user preferences and user programs. The computer system 2201 in some cases can include one or more additional data storage units that are external to the computer system 2201, such as located on a remote server that is in communication with the computer system 2201 through an intranet or the Internet.

The computer system 2201 can communicate with one or more remote computer systems through the network 2230. For instance, the computer system 2201 can communicate with a remote computer system of a user (e.g., an operator, a patient, etc.). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2201 via the network 2230.

Methods as described herein can be implemented by way of machine (e.g., computer processor) executable code stored on an electronic storage location of the computer system 2201, such as, for example, on the memory 2210 or electronic storage unit 2215. The machine executable or machine readable code can be provided in the form of software. During use, the code can be executed by the processor 2205. In some cases, the code can be retrieved from the storage unit 2215 and stored on the memory 2210 for ready access by the processor 2205. In some situations, the electronic storage unit 2215 can be precluded, and machine-executable instructions are stored on memory 2210.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2201 can include or be in communication with an electronic display 2235 that comprises a user interface (UI) 2240 for providing, for example, patient image input data and/or tissue remodeling risk assessment output data as described herein. Examples of UI's include, without limitation, a graphical user interface (GUI) and web-based user interface. FIGS. 4-17 show exemplary user interface which may be provided to the user on the display. Data input by a user (e.g., mole boundary selection, etc.) into the user interface may be sent to the processor. The processor may be configured with instructions to run the image processing and scoring algorithms as described herein to generate one or more outputs. The output(s) of the processing and/or scoring algorithms may be sent by the processor to a display which displays the outputs to a user with the user interface.

Methods and systems of the present disclosure can be implemented by way of one or more algorithms. An algorithm can be implemented by way of software upon execution by the central processing unit 2205. The algorithm can, for example, select an optimal image pair, segment one or more images for analysis, compare visual features on the images, score the image pair, etc. as described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for assessing tissue remodeling risk, comprising:

(a) collecting a plurality of images of a lesion located in a target region of a subject's skin, wherein the plurality of images comprises (1) a set of visible light images of the lesion and (2) a set of fluorescent images of the lesion, wherein a fluorescent marker is configured to provide fluorescence when bound to one or more biomarkers associated with tissue remodeling; and (b) using at least one processor and a non-transitory computer readable storage medium encoded with a computer program:

(I) processing the plurality of images to determine an optimal image pair for the target region, wherein the optimal image pair comprises: (i) a visible light image selected from (1), and (ii) a fluorescent image selected from (2), wherein the optimal image pair is determined automatically using the at least one processor based on (i) a position of the lesion within each of the set of visible light images and each of the set of fluorescent images, (ii) a degree of similarity or correlation between each of the set of visible light images and each of the set of fluorescent images, and (iii) a focus quality of each of the set of visible light images and each of the set of fluorescent images, wherein the visible light image comprises a first set of visual characteristics, wherein the fluorescent image comprises a second set of visual characteristics, wherein at least a portion of the second set of visual characteristics is not visible in the first set of visual characteristics, and wherein at least a portion of the first set of visual characteristics is not visible in the second set of visual characteristics;

(II) segmenting the visible light image to identify a border of the lesion, wherein the segmenting of the visible light image comprises converting the visible light image into an intensity image;

(III) adding the border of the lesion identified from the visible light image to the fluorescent image based on a location of the fluorescent marker;

(IV) generating an assessment of the target region based at least on the optimal image pair, wherein the generating of the assessment of the target region comprises evaluating an aggregate score for the optimal image pair, wherein the aggregate score comprises a visible score for the visible light image and a fluorescent score for the fluorescent image, wherein the visible score is based on a first set of metrics associated with the first set of visual characteristics in the visible light image, wherein the first set of metrics comprises one or more of the following: size, shape, volume, color, or surface texture of the lesion and its surrounding area, wherein the fluorescent score is based on a second set of metrics associated with the second set of visual characteristics in the fluorescent image, and wherein the second set of metrics comprises one or more of the following: size, shape, area or extent of tissue remodeling, pixel intensity, fluorescence intensity, patterns or texture in the target region beneath the subject's skin and surrounding the lesion, wherein the visible score comprises one or more measures of asymmetry, border irregularity, color variegation, and diameter of the lesion based at least in part on the border of the lesion identified by the segmenting in (II), and wherein the fluorescent score comprises one or more measures of intensity and texture of fluorescence in the fluorescent image based at least in part on the border of the lesion added to the fluorescent image in (III); and (V) displaying on a graphical user interface the assessment, the optimal image pair, and a schematic showing a location of the target region on the subject's body, wherein the assessment of the target region is indicative of a probability of tissue remodeling at the target region.

2. The method of claim 1, wherein the lesion comprises a mole on the subject's skin.

3. The method of claim 1, wherein the visible light image and the fluorescent image are selected to be complementary or matching with each other.

4. The method of claim 2, wherein the first set of visual characteristics is associated with the mole and the skin of the subject, and wherein the second set of visual characteristics is associated with underlying tissue beneath the skin and surrounding the mole.

5. The method of claim 1, wherein the optimal image pair is a first optimal image pair, and wherein after (I) and prior to (IV) the method further comprises:

displaying an option on the graphical user interface to a user, wherein the option permits the user to accept or reject the first optimal image pair; and receiving an input from the user in response to the option displayed on the graphical user interface.

6. The method of claim 5, further comprising:

processing the plurality of images to determine a second optimal image pair for the target region when the input is indicative of the user rejecting the first optimal image pair, wherein the second optimal image pair is different from the first optimal image pair.

7. The method of claim 5, comprising: continuing with (IV) and (V) when the input is indicative of the user accepting the first optimal image pair.

8. The method of claim 5, further comprising:

processing the plurality of images to determine a plurality of other optimal image pairs for the target region when the input is indicative of the user rejecting the first optimal image pair; and displaying the plurality of other optimal image pairs on the graphical user interface.

9. The method of claim 2, wherein the probability of tissue remodeling is associated with a probability of development of melanoma in the mole, and wherein the assessment is useable to determine a clinical diagnosis or course of action based on the probability of development of melanoma in the mole.

10. The method of claim 1, wherein the segmenting of the visible light image is used to generate the first set of metrics.

11. The method of claim 1, wherein the visible light image and the fluorescent image are adjusted and aligned to a set of coordinates within the optimal image pair.

12. The method of claim 1, further comprising: comparing the optimal image pair to one or more reference images.

13. The method of claim 12, wherein the one or more reference images comprise a reference image pair.

14. The method of claim 13, wherein the reference image pair comprises (1) a visible light reference image that is not from the set of visible light images and (2) a fluorescent reference image that is not from the set of fluorescent images.

15. The method of claim 13, wherein the optimal image pair comprises fiducials, and wherein the reference image pair does not comprise fiducials.

16. The method of claim 13, wherein the optimal image pair comprises a first set of fiducials that are located at a predefined location and/or orientation relative to the lesion, and wherein the reference image pair comprises a set of fiducials that are located near a boundary of each reference image within the reference image pair.

17. The method of claim 1, wherein the generating of the assessment of the probability of tissue remodeling is performed automatically by the at least one processor.

18. The method of claim 1, further comprising segmenting the fluorescent image, wherein the segmenting of the fluorescent image is used to generate the second set of metrics, and wherein the segmenting of the fluorescent image comprises segmenting the fluorescent image into a plurality of zones surrounding the target region.

* * * * *